(12) United States Patent
Luchoomun et al.

(10) Patent No.: US 6,881,860 B2
(45) Date of Patent: Apr. 19, 2005

(54) COMPOUNDS AND METHODS TO INCREASE PLASMA HDL CHOLESTEROL LEVELS AND IMPROVE HDL FUNCTIONALITY

(75) Inventors: Jayraz Luchoomun, Lilburn, GA (US); Charles Q. Meng, Alpharetta, GA (US); Uday Saxena, Atlanta, GA (US); James A. Sikorski, Alpharetta, GA (US)

(73) Assignee: Atherogenics, Inc., Alpharetta, GA (US)

( * ) Notice: Subject to any disclaimer, the term of this patent is extended or adjusted under 35 U.S.C. 154(b) by 160 days.

(21) Appl. No.: 09/833,407

(22) Filed: Apr. 11, 2001

(65) Prior Publication Data

US 2002/0016364 A1 Feb. 7, 2002

Related U.S. Application Data

(60) Provisional application No. 60/196,201, filed on Apr. 11, 2000.

(51) Int. Cl.$^7$ ............................................. C07C 321/00
(52) U.S. Cl. ...................................... 562/426; 514/568
(58) Field of Search ........................... 562/426; 514/568

(56) References Cited

U.S. PATENT DOCUMENTS

| | | |
|---|---|---|
| 4,076,841 A | 2/1978 | Wagner et al. |
| 5,262,439 A | 11/1993 | Parthasarathy |
| 5,294,724 A | 3/1994 | Jendralla et al. |
| 5,627,205 A | 5/1997 | Regnier et al. |
| 5,770,355 A | 6/1998 | Brocia et al. |
| 6,121,319 A | 9/2000 | Somers |
| 6,147,250 A | 11/2000 | Somers |
| 6,323,359 B1 | 11/2001 | Jass |
| 6,448,019 B1 | 9/2002 | Mendelsohn et al. |

FOREIGN PATENT DOCUMENTS

| | | |
|---|---|---|
| EP | 212 310 A2 | 3/1987 |
| EP | 254 272 A2 | 1/1988 |
| EP | 292 660 A2 | 11/1988 |
| EP | 348 203 A1 | 12/1989 |
| EP | 418 648 A1 | 3/1991 |
| FR | 2.130.975 | 11/1972 |
| FR | 2.133.024 | 11/1972 |
| FR | 2.134.810 | 12/1972 |
| FR | 2.140.769 | 1/1973 |
| FR | 2.168.137 | 8/1973 |
| WO | WO 95/30415 A1 | 11/1995 |
| WO | US 96/08239 A | 3/1996 |
| WO | WO 96/08239 | 3/1996 |
| WO | WO 97/26258 A1 | 7/1997 |
| WO | WO 98/30255 A2 | 7/1998 |
| WO | WO 98/51289 A2 | 11/1998 |
| WO | WO 98/51662 A2 | 11/1998 |
| WO | 98/51662 * | 11/1998 |
| WO | WO 99/24400 A1 | 5/1999 |
| WO | WO 00/26184 A1 | 5/2000 |
| WO | WO 00/28332 A1 | 5/2000 |

OTHER PUBLICATIONS

Rinninger et al.; Probucol Enhances Selective Uptake of HDL–Associated Cholesteryl Esters in Vitro by a Scavenger Receptor B–I–Dependent Mechanism; Arterioscler Thromb Vasc Biol.; Abstract XP 008001008; (1999); vol. 19, No. 5; pp. 1325–1332.

Combettes–Souverain et al.; SR–BI et métabolisme du cholestérol; Médecine Sciences; Abstract XP 008001010; (Nov. 1999); vol. 15, No. 11; pp. 1252–1258.

Meta et al.; Human Apolipoprotein A–I Gene Promoter Mutation Influences Plasma Low Density Lipoprotein Cholesterol Response to Dietary Fat Saturation; Atherosclerosis; Abstract XP–001061299; (1998); vol. 137 pp. 367–376.

Funke et al; Uptake of Apolipoprotein E–Containing High Density Lipoproteins by Hepatic Parenchymal Cells; Arteriosclerosis; Abstract XP 002001004; Sep./Oct., 1984); vol. 4, No. 5; pp. 452–461.

Miller et al; Apolipoprotein A–$I_{Zavalla}$ ($Leu_{159} \rightarrow Pro$) HDL Cholesterol Deficiency in a Kindred Associated With Premature Coronary Artery Disease; Arterioscler Thromb Vasc Biol.; Abstract XP 008001006; (1998); vol. 18, No. 8; pp. 1242–1247.

Pfeuffer et al.; Probucol Increases the Selective Update of HDL Cholesterol Esters by Hep G2 Human Hepatoma Cells; Arteriosclerosis and Thrombosis; Abstract XP 008001007; (1992); vol. 12, No. 7; pp. 870–878.

Mao et al., "Antioxidant Activity of Probucol and Its Analogues in Hypercholesterolemic Watanabe Rabbits," *Journal of Medicinal Chemistry*, Jan. 1991, Vol. 34, No. 1, pp. 298–302.

Mao et al. "Attenuation of Atherosclerosis in a Modified Strain of Hypercholesterolemic Watanabe Rabbits with Use of a Probucol Analogue (MDL29,311) That Does Not Lower Serum Cholesterol," *Arteriosclerosis and Thrombosis*, Sep./Oct. 1991, vol. 11, No. 5, pp. 1266–1275.

Ramasamy, Santhini et al., "Modulation of Expression of Endothelial Nitric Oxide Synthase by Nordihydroguaiaretic Acid, A Phenolic Antioxidant in Cultured Endothelial Cells," *Molecular Pharmacology*, Apr. 5, 1999, vol. 56, pp. 116–123.

(Continued)

Primary Examiner—Paul J. Killos
(74) Attorney, Agent, or Firm—Sherry M. Knowles; King & Spalding, LLP

(57) ABSTRACT

It has been discovered that certain selected ethers of probucol, and their pharmaceutically acceptable salts or prodrugs, are useful for increasing circulating HDL cholesterol. These compounds may also improve HDL functionality by (a) increasing clearance of cholesteryl esters, (b) increasing HDL-particle affinity for hepatic cell surface receptors or (c) increasing the half life of apoAI-HDL.

33 Claims, 5 Drawing Sheets

OTHER PUBLICATIONS

Chemical Abstract, Database Chemabs Online!, Chemical Abstracts Service, Columbus, Ohio, US, STN, Accession No. 127:75973, XP002115597, see abstract; RN 1706–68–9 & V.Z. Lankin et al.: DOKL. AKAD. NAUK, V. 351, No. 4, 1996, pp. 554–557.

Chemical Abstract, Database Chemabs Online!, Chemical Abstracts Service, Columbus, Ohio, US, STN, CAPLUS Accession No. 1970:445047, XP002124423, see abstract; RN 27428–10–0, 27428–13–3, 27428–14–4, 27428–15–5, 27428–16–6, 27428–17–7, 27428–18–8, 27428–19–9 & M. B. Neuworth et al.: J. Med. Chem., V. 13, No. 4, 1970, pp. 722–725.

Chemical Abstract, Database Chemabs Online!, Chemical Abstracts Service, Columbus, Ohio, US, STN, CAPLUS Accession No. 1986:28675, XP002124424, see abstract; RN 99661–86–6, 99661–87–7, 27466–44–0 & Chemical Abstracts, vol. 104, No. 5, Feb. 3, 1986, Columbus, Ohio, US; Abstract No. 28675, abstract & P. De Meglio et al.: Farmaco, Ed. Sci., vol. 40, No. 11, 1985, pp. 833–844.

Cominacini et al., "Antioxidants Inhibit the Expression of Intercellular Cell Adhesion molecule–1 and Vascular Cell Adhesion Molecule–1 Induced by Oxidized LDL on Human Umbilical Vein Endothelial Cells," *Free Radical Biology & Medicine*, vol. 22, Nos. 1/2, pp. 117–127, 1997.

Feldman, Davis, et al., "The In Vitro and Ex Vivo Antioxidant Properties, and Hypolipidemic Activity of CGP 2881," *Atherosclerosis*, Dec. 28, 1998, vol. 144, pp. 343–355.

Fruebis, Joachim, "A Comparison of the Antiatherogenic Effects of Probucol of a Structural Analogue of Probucol in Low Density Lipoprotein Receptor–deficient Rabbits," *The American Society for clinical Investigation, Inc.*, Jul. 1994, vol. 94, pp. 392–398.

Meng et al.; Novel Phenolic Antioxidants as Multifunctional Inhibitors of Inducible VCAM–1 Expression for Use in Antherosclerosis, *Bioorganic & Medicinal Chemistry Letters*; (2002); pp. 2545–2548.

Rinninger et al.; "Probucol Enhances Selective Uptake of HDL–Associated Cholesteryl Esters In Vitro by a Scavenger Receptor B–I–Dependent Mechanism," *Artherioscler Thromb Vasc Biol.*; (1999); vol. 19; pp. 1325–1332.

Sawayama, et al.; "Effects of Probucol and Pravastatin on Common Carotid Atherosclerosis in Patients with Asymptomatic Hypercholesterolemia," *Journal of the American College of Cardiology*; vol. 39; No. 4; (2002); pp. 610–616.

* cited by examiner

Effect of Compound A on HDL cholesterol in Cholesterol-fed Hamsters
*Two Week Dosing*

In vitro apoAI HDL elevation

COMPOUNDS AND METHODS TO INCREASE PLASMA HDL CHOLESTEROL LEVELS AND IMPROVE HDL FUNCTIONALITY

This application claims priority to U.S. Ser. No. 60/196,201, filed on Apr. 11, 2000.

This invention is in the area of compounds, compositions, and methods to increase plasma high density lipoprotein cholesterol levels, and to improve the functionality of circulating high density lipoprotein.

BACKGROUND OF THE INVENTION

Coronary heart disease (CHD) remains the leading cause of death in the industrialized countries. The primary cause of CHD is atherosclerosis, a disease characterized by the deposition of lipids, including cholesterol, in the arterial vessel wall, resulting in a narrowing of the vessel passages and ultimately hardening of the vascular system. Epidemiological studies have demonstrated an inverse relationship between serum high density lipoprotein cholesterol (HDLc) levels and the incidence of CHD (Castelli, W. P. et al., *J. Am. Med. Assoc.*, 256, 2835 (1986); Miller and Miller *Lancet*, 1, 16 (1975); Gordon et al., *Circulation* 79, 8 (1989)). Low levels of HDLc represent a significant independent CHD risk factor whether or not these patients have elevated low density lipoprotein cholesterol (LDLc) levels (Kannel, W. B., *Am. J. Cardiol.* 76, 69c (1995)). Indeed, high density lipoprotein (HDL) is recognized as the anti-atherogenic lipoprotein (Stein, O. and Stein, Y., *Atherosclerosis* 144, 28 (1999)). Several clinical studies have demonstrated reduced CHD events with treatments that raised HDLc. For example, the recent VA-HIT trial showed for the first time that by raising HDL cholesterol without affecting LDL cholesterol, cardiac events in patients with CHD were substantially reduced (Rubins, H. B. and Robins, S., *Am. J. Cardiol.* 86, 543 (2000)). Every 1% rise in HDLc, produced a corresponding 2–3% decrease in CHD.

Atherosclerosis generally begins with local injury to the arterial endothelium followed by proliferation of arterial smooth muscle cells from the medial layer to the intimal layer along with the deposition of lipid and accumulation of foam cells in the lesion. As the atherosclerotic plaque develops it progressively occludes more and more of the affected blood vessel and can eventually lead to ischaemia or infarction. Because deposition of circulating lipids such as cholesterol plays a major role in the initiation and progression of atherosclerosis, it is important to identify compounds, methods and compositions to help remove cholesterol from the developing peripheral tissues, including atherosclerotic plaque. As described below, HDL promotes reverse cholesterol transport, a process by which excess cholesterol is extracted from peripheral cells by HDL and delivered to the liver for its elimination. Thus, it is important to identify compounds, methods and compositions that can increase HDLc (*Euro. Heart J.* 2001 March 15; 22(6), 465–471) and improve the functionality of HDL (K. Alam et al., *J. Biol. Chem.* 2001, in press).

Circulating lipoproteins serve as vehicles for the transport of water-insoluble lipids like cholesteryl esters, triglycerides and the more polar phospholipids and unesterified cholesterol in the aqueous environment of plasma (Bradely, W. A. and Gotto, A. M.: American Physiological Society, Bethesda, Md., pp 117–137 (1978)). The solubility of these lipids is achieved through physical association with proteins termed apolipoproteins, and the lipid-protein complexes are called lipoproteins (Dolphin, P. J., *Can. J Biochem. Cell. Biol.* 63, 850–869 (1985)). Five distinct classes of lipoproteins have been isolated from human plasma: chylomicrons, very low density lipoproteins (VLDL), low density lipoproteins (LDL), high density lipoproteins (HDL) and lipoprotein) (a (LP(a)). (Alaupovic, P. (1980) In Handbook of Electrophoresis. Vol. 1, pp. 27–46; Havel, R. J., Eder, H. A.; Bragdon, J. H., *J. Clin. Invest.* 34, 1343 (1955)).

HDL particles are first secreted from the liver and intestine as small, discoidal particles called "pre-beta 1" HDL. HDL particles undergo a continuous interconversion in the plasma beginning with the conversion of the "nascent discoidal "pre-beta 1" HDL into spherical HDL3, through the action of plasmatic enzymes, mainly lecithin-cholesteryl acyltransferase (LCAT), that converts free cholesterol to cholesteryl ester (Glomset J. A., and Norum K. R., *Advan. Lipid Res.*, 11, 1–65, (1973)); McCall, M. R., Nichols, A. V., Morton, R. E., Blanche, P. J., Shore, V. G., Hara, S. and Forte, T. M., *J. Lipid Res.* 34, 37 (1993)). HDL3 acquires phospholipids (PL) and free cholesterol (FC) in the presence of other plasmatic enzymes such as lipoprotein lipase (LPL) (Patsch, J. R., Gotto, A. M., Olivercrona, T. and Eisenberg, S., *Proc. Natl. Acad. Sci.*, 75, 4519 (1978)), and further action of LCAT helps form large CE-rich HDL which constitute the CE-rich HDL2 subpopulation (McCall, M. R., et al., *J. Lipid Res.* 34, 37 (1993)). Mature HDL is spherical and contains various amounts of lipids and apolipoprotein. Apolipoprotein A-I (apoAI) is the major protein component of mature HDL, and most of the cholesterol associated with HDL is esterified as cholesteryl esters (CE). HDL is believed to play a fundamental functional role in the transport of lipids and represents a site for storage of potentially harmful lipids and apolipoproteins which if unregulated could have harmful effects including changing cellular functions, altering gene expression, and obstructing blood flow by narrowing the vessel lumen. apoAI has been found to be more powerful as a marker for coronary disease than the cholesterol component of HDL (Maciejko J. J. et al., *New England J. Med.* 309, 385–389 (1983)). However, HDLc remains an important independent predictor of atherosclerosis, and HDLc is an important predictor of survival in post coronary artery bypass graft patients as a result of the 20-year experience from The Cleveland Clinic Foundation ((Foody J M et al. (2000) Circulation, 102 (19 suppl3), III90–94). Clinical surveys have confirmed that elevated HDLc is favorable in preventing the development of atherosclerotic lesion and low levels of HDLc together with low apoAI levels are currently considered to be the most reliable parameters in predicting the development of atherosclerosis in hyperlipidemic patients ((Mingpeng s and Zongli W, (1999) Experimental Gerontology, 34 (4); 539–48)).

Reverse Cholesterol Transport

HDL promotes reverse cholesterol transport, a process by which excess cholesterol is extracted from peripheral cells by HDL and delivered to the liver for its elimination. Reverse cholesterol transport, therefore, reduces cholesterol accumulation in the artery wall (Reichl, D and Miller, N. E., *Arteriosclerosis* 9, 785 (1989)). Because there is no cholesterol accumulation in extrahepatic organs, cholesterol must be transported to the liver by HDL for ultimate excretion into bile, either as free cholesterol, or as bile acids that are formed from cholesterol (Kwiterovich, P. O., *Amer. J. Cardiol.* 82, 13Q, (1998)). HDL may acquire part of its anti-atherogenic character by promoting the reverse transport of cholesterol. Because promoting the reverse transport of cholesterol leads to removal of cholesteryl esters and anti-atherogenic effects, it is important to discover new compounds that promote the reverse transport process. One potential target for promoting reverse transport is apoAI, because increased apoAI would allow more efflux of cholesterol from peripheral tissues, including atherosclerotic lesions, and also improve the functionality of circulating HDL. The major functional role of HDL is to remove cholesterol from peripheral tissues including atherosclerotic lesions and taking cholesterol in its ester form to the liver for elimination. It would therefore be desirable to improve the functionality of HDL by acting on proteins and receptors involved in RCT in such a way as to increase the half life of apoAI-HDL and/or to increase the delivery of cholesteryl esters to the liver.

Reverse cholesterol transport involves several steps that are important for the transport of cholesterol from artery walls and in general from peripheral cells to the liver. The first step is the efflux of cholesterol from peripheral tissues to nascent and circulating HDL particles (Fielding C. J. and Fielding P. E, *J. Lipid. Res.* 36, 211 (1995); Rothblat G. H., de la Llera-Moya, M., Atger, V., Kellner-Weibel, G., Williams, D. L., and Phillips, M. C., *J. Lipid Res.* 40, 781 (1999)). Recent findings suggest that ABC1 (ATP-cassette binding protein 1) plays a crucial role in that process (Gura, T., *Science* 285, 814 (1999)). The second step involves the plasmatic modulation of HDL that loads cholesterol from peripheral cells, and the interactions with plasmatic enzymes and proteins that modulate plasma HDL concentrations during this process. One major enzyme known as lecithin-cholesteryl acyltransferase (LCAT) and its cofactor apoAI promote the esterification of free cholesterol to cholesteryl ester, which is then packaged into the core of the HDL (Kwiterovich, P. O., *Amer. J. Cardiol.* 82, 13Q (1998)). LCAT function maintains a concentration gradient (Francone et al., *J. Biol. Chem.* 264, 7066 (1989)). Cholesteryl ester transfer protein (CETP) helps shuttle excess cholesteryl ester from HDL to triglyceride-rich lipoproteins in exchange for triglycerides (Eisenberg, *J. Lipid Res.* 26, 487 (1985); Morton, R. E., and Zilversmit D. B., *J. Biol. Chem.*, 258, 11751 (1983)). The last step of the reverse cholesterol transport involves the movement of cholesterol in its esterified form from HDL to the liver and from there into the bile, either directly or after conversion to bile acids, for ultimate elimination.

Numerous efforts are being made to understand the process of reverse cholesterol transport and the underlying mechanisms of cholesterol and cholesteryl ester exchange between cellular surfaces and HDL. The cholesteryl esters at the core of the HDL may be delivered to the liver for elimination by several mechanisms. First, the receptor independent model explains diffusion as a process for both the uptake and the eflux of free cholesterol (Rothblat, G. H. et al., *J. Lipid Res.*, 40, 781 (1999)). Second, cholesteryl ester transfer protein moves cholesteryl ester from HDL to the triglyceride rich lipoproteins and very low density lipoprotein. The cholesteryl esters are then taken up by the liver through the LDL receptor pathway. Third, if the cholesteryl ester transfer protein activity is low, large apolipoprotein-E containing HDL particles may be cleared via the LDL receptor pathway. Fourth, cholesteryl ester may be selectively removed from HDL by an HDL receptor on the liver (Kwiterovich, P. O., *Amer. J. Cardiol.* 82, 13Q (1998); Arbeeny, C. M. et al., *Biochem. Biophys. Acta.* 917, 9 (1987)).

The receptor-dependent model accounts for HDL-binding proteins, such as class B, type I and type II scavenger receptors (SR-BI and SR-BII) which can mediate the selective uptake of HDL cholesteryl esters to the liver and steroidogenic tissues (Acton, S. et al., *Science* 271, 518 (1996); Murao, K. et al., *J. Biol. Chem.* 272, 17551 (1997); Webb, N. R. et al.,*J. Biol. Chem.* 273, 15241 (1998)). It has been postulated that HDL binds to SR-BI at the cell surface via direct interaction between SR-BI and the amphipathic helical repeats of apolipoprotein A-I providing a water-depleted "channel" that allows cholesteryl ester (CE) molecules to diffuse from CE-rich HDL to the cell plasma membrane (Williams, D. L. et al., *Current Opinion Lipidology*, 10, 329 (1999); Rodrigueza W. V. et al., *J. Biol. Chem.* 274, 20344 (1999)). Mice with genetically manipulated SR-BI expression and the murine adrenal Y1-BS1 cell line have been useful in defining the role of SR-BI in HDL metabolism. HDL cholesterol levels are increased in animals deficient in SR-BI indicating the importance of SR-BI in the clearance of HDL cholesterol. However, activating the reverse cholesterol transport system through increased SRB-1 expression is a potential way to reduce atherogenesis if HDLc is not significantly reduced (Ueda, Y., Gong, E., Royer, L., Cooper, P. N., Francone, O. L., and Rubin E. M., *J. Biol. Chem.*, 275, 27, 20368 (2000)). Therapeutic interference with HDL metabolism that will bring changes in the kinetics and functionality of HDL rather than plasma HDL cholesterol levels per se will reduce atherogenesis (Eckardstein, V., and Assmann, G., *Current Opinion in Lipidology*, 11, 627 (2000)). Therapeutic intervention that will increase HDL cholesterol and in addition improve HDL kinetics and functionality, will significantly reduce atherogenesis.

HDL catabolism by SR-B1 does not involve HDL holoprotein particle uptake and lysosomal degradation of apolipoproteins. This is supported by the finding that transgenic mice deficient in SR-B1 display elevated HDLc yet exhibit no change in levels of plasma apoAI (Rigotto, et al., *Proc. Natl. Acad. Sci.*, 94, 12610 (1994)) Endocytosis and lysosomal degradation of HDL holoprotein is known to occur (Steinberg, D. Science, 274, 460 (1996)), but endocytic HDL receptors have remained elusive. A recently characterized receptor, cubilin, has been found to mediate HDL holoparticle endocytosis (Hammad et al., *Proc. Natl. Acad. Sci.*, 96, 10158 (1999)). A similar protein or putative receptor, still remains to be found, that could be responsible for hepatic clearance of HDL holoproteins.

In humans, low HDL cholesterol levels may relate to defects in synthesis or catabolism of apoAI, with catabolic defects being more common (Brinton, E. A., et al., *Aterio-sclerosis Thromb.* 14, 707 (1994)); Fridge, N., et al., *Metabolism* 29, 643 (1980)). Low HDL is often associated with hypertriglyceridemia, obesity, and insulin resistance (Brinton, E. A., et al., *Ateriosclerosis Thromb.* 14, 707 (1994)). HDL from hypertriglyceridemic subjects characterized by low HDL levels have small HDL particles which are susceptible to renal filtration and degradation. The liver is the principal organ of HDL apolipoprotein degradation (Horowitz, B. S., et al., *J. Clin. Invest.* 91, 1743 (1993)).

HDL has other important characteristics that may contribute to its anti-atherogenic properties. Recent evidence suggests that HDL may have antioxidant and antithrombotic properties (Tribble, D., et al., *J. Lipid Res.* 36, 2580 (1995); Mackness, M. I., et al., *Biochem. J.* 294, 829 (1993); Zeither, A. M., et al., *Circulation* 89, 2525 (1994)). HDL may also affect the production of some cell adhesion molecules such as vascular cell adhesion molecule-1 (VCAM-1) and inter-cellular adhesion molecule-1 (ICAM-1), (Cockerill, G. W., et al., *Arterioscler. Thromb.*, 15, 1987 (1995)). These properties of HDL also provide protection against coronary artery disease.

Existing Lipid Therapies

Therapeutic agents that elevate HDL, are prime targets for drug development, given the evidence in favor of HDL and its protective function against atherosclerosis. Towards this end, one pathway targeted by industry has been to increase synthesis and secretion of apolipoprotein A-I (apoAI), the major protein in HDL.

U.S. Pat. No. 5,968,908 discloses analogs of 9-cis-retinoic acid and their use to raise HDLc levels by increasing the synthesis of apoAI.

U.S. Pat. No. 5,948,435 discloses a method of regulating cholesterol related genes and enzymes by administering lipid acceptors such as liposomes. Additionally, U.S. Pat. No. 5,746,223 discloses a method of forcing the reverse transport of cholesterol by administering liposomes.

Several known agents such as Gemfibrozil (Kashyap, A., *Art. Thromb. Vasc. Biol.* 16, 1052 (1996)) increase HDLc levels. Gemfibrozil is a member of an important class of drugs called fibrates that act on the liver. Fibrates are fibric acid derivatives (bezafibrate, fenofibrate, gemfibrozil and clofibrate) which profoundly lower plasma triglyceride levels and elevate HDLc (Sirtori C. R., and Franceschini G., *Pharmac Ther.* 37, 167 (1988); Grundy S. M., and Vega G. L. *Amer. J Med.* 83, 9 (1987)). The typical clinical use of fibrates is in patients with hypertriglyceridemia, low HDLc and combined hyperlipidemia.

The mechanism of action of fibrates is not completely understood but involves the induction of certain apolipoproteins and enzymes involved in VLDL and HDL metabolism. For example, cholesteryl ester transfer protein activity is reduced by fenofibrate, gemfibrozil, phentyoin and alcohol.

Ethanol is known to increase HDLc levels and has been found to decrease coronary disease risk (Klatsky, A. L., et al., *Intern. Med.* 117, 646 (1992)). Regular use of alcohol has been shown to be correlated with increases in serum apoAI and HDL cholesterol levels. These increases are believed to be related to liver cytochrome P450 induction (Lucoma, P. V., et al., Lancet 1, 47 (1984)).

Nicotinic acid (niacin), a water-soluble vitamin has a lipid lowering profile similar to fibrates and may target the liver. Niacin has been reported to increase apoAI by selectively decreasing hepatic removal of HDL apoAI, but niacin does not increase the selective hepatic uptake of cholesteryl esters (Jin, F. Y., et al., *Arterioscler. Thromb. Vasc. Biol.* 17, 2020 (1997)).

In addition, premenopausal women have significant cardio-protection as a result of high HDLc levels, probably due to estrogens. Tam et al. have shown that human hepatoma cells increased apoAI mass in culture medium when cells were treated with estrogen (Tam S. P., et al., J. Biol. Chem. 260, 1670 (1985); Jin, F. Y., et al., Arterioscler. Thomb. Vasc. Biol. 18, 999 (1998)). Dexamethasone, prednisone, and estrogen activate the apoAI gene, increase apoAI and HDL cholesterol, reduce lipoprotein B, and reduce LDL cholesterol (Kwiterovich, P. O. *Amer. J. Cardiol.* 82, 13Q (1998)). The side effects of such steroids are well known and limit their chronic use in atherosclerosis.

Diet contributes up to 40% of cholesterol that enters through the intestine and bile contributes the rest of the "exogenous" cholesterol absorbed through the intestine (Wilson M. D., and Rudel L. L. *J. Lipid Res.* 35, 943 (1994)). Decreasing dietary cholesterol absorption therefore is a regulatory point for cholesterol whole body homeostasis. Cholesterol absorption inhibitors lower plasma cholesterol by reducing the absorption of dietary cholesterol in the gut or by acting as bile acid sequestrants (Stedronsky, E. R., *Biochim. Biophys. Acta* 1210, 255 (1994)).

Cholesterol lowering agents decrease total plasma and LDL cholesterol and some may increase HDLc. Several such agents, which primarily reduce LDL cholesterol, are discussed because of an associated slight increase in HDLc levels. For example, statins represent a class of compounds that are inhibitors of HMG CoA reductase, a key enzyme in the cholesterol biosynthetic pathway (Endo, A., In: Cellular Metabolism of the Arterial Wall and Central Nervous System. Selected Aspects. Schettler G, Greten H, Habenicht A. J. R. (Eds.) Springer-Verlag, Heidelberg (1993)).

The statins decrease liver cholesterol biosynthesis, which increases the production of LDL receptors thereby decreasing total plasma and LDL cholesterol (Grundy, S. M. *New Engl. J. Med.* 319, 24 (1988); Endo, A., *J. Lipid Res.* 33, 1569 (1992)). Depending on the agent and the dose used, statins may decrease plasma triglyceride levels and some may increase HDLc. Currently the statins on the market are lovastatin (Merck), simvastatin (Merck), pravastatin (Sankyo and Squibb) and Fluvastatin (Sandoz). A fifth statin, atorvastatin (Parke-Davis/Pfizer), is the most recent entrant into the statin market. Statins have become the standard therapy for LDL cholesterol lowering. The statins are effective LDLc lowering agents but have some side effects, the most common being increases in serum enzymes (transaminases and creatinine kinase). In addition, these agents may also cause myopathy and rhabdomyolysis especially when combined with fibrates. Because of possible side effects of LDLc lowering drugs, it is important to discover novel compounds that possess antiatherogenic characteristics such as increasing HDLc levels and HDL functionality without raising LDLc levels.

Another drug that in part may impact the liver is probucol (Zimetbaum, P., et al., *Clin. Pharmacol.* 30, 3 (1990)). Probucol is used primarily to lower serum cholesterol levels in hypercholesterolemic patients and is commonly administered in the form of tablets available under the trademark Lorelco™. Probucol is chemically related to the widely used food additives 2,[3]-tert-butyl-4-hydroxyanisole (BHA) and 2,6-di-tert-butyl-4-methyl phenol (BHT). Its full chemical name is 4,4'-(isopropylidenedithio) bis(2,6-di-tert-butylphenol). Probucol is a lipid soluble agent used in the treatment of hypercholesterolemia including familial hypercholesterolemia (FH). Probucol reduces LDL cholesterol typically by 10% to 20%, but it also reduces HDLc by 20% to 30%. The drug has no effect on plasma triglycerides. The mechanism of action of probucol in lipid lowering is not completely understood. The LDLc lowering effect of probucol may be due to decreased production of apoB containing lipoproteins and increased clearance of LDL. Probucol lowers LDLc in the LDL-receptor deficient animal model (WHHL rabbits) as well as in FH populations. Probucol has been shown to actually slow the progression of atherosclerosis in LDL receptor-deficient rabbits as discussed in Carew et al. (1987) *Proc. Natl. Acad. Sci. U.S.A.* 84:7725–7729. The HDLc lowering effect of probucol may be due to decreased synthesis of HDL apolipoproteins and increased clearance of this lipoprotein. High doses of probucol are required in clinical use.

U.S. Pat. No. 6,004,936 to Robert Kisilevsky describes a method for potentiating the release and collection of cholesterol from inflammatory or atherosclerotic sites in vivo, the method including the steps of increasing the affinity of high-density lipoprotein for macrophages by administering to a patient an effective amount of a composition comprising a compound selected from the group consisting of native serum amyloid A (SAA) and a ligand having SAA properties thereby increasing the affinity of high density lipoprotein (HDL) for macrophages and potentiating release and collection of cholesterol.

U.S. Pat. Nos. 5,821,372 and 5,783,707 to Elokdah et al. describe 2-thioxo-imidazolidin-4-one derivatives that are useful for increasing blood serum HDL levels.

U.S. Pat. No. 6,171,849 to Rittersdorf et al. discloses an apparatus comprising a first porous carrier and a second porous carrier for evaluating biological fluid samples. The apparatus is used for separating non high density lipoprotein (non-HDL) from a lipoprotein in a body sample and for determining high density lipoprotein (HDL) cholesterol in a HDL and non high density lipoprotein (non-HDL) in a body sample.

European Patent Publication 1029928 A2 to Watanabe, Motokazu et al. discloses a method for determining cholesterol in low density lipoprotein comprising the steps of (a) measuring total cholesterol level in a sample containing at least high density lipoprotein, low density lipoprotein, very low density lipoprotein and chylomicron, and (b) measuring cholesterol levels in the high density lipoprotein, very low density lipoprotein and chylomicron in the sample, wherein the cholesterol level in the low density lipoprotein is determined by subtracting a value obtained in the step (b) from a value obtained in the step (a). The invention enables concurrent determination of cholesterol level in low density lipoprotein and total cholesterol level, facilitating acquisition of two types of biological information at a time.

International application WO 01/7388 A1 to Sugiuchi describes a method for fractional quantification of cholesterol in low density lipoproteins; a quantification reagent to be used; a method for continuous fractional quantification of cholesterol in high density lipoproteins and cholesterol in low density lipoproteins; a reagent kit to be used; a method for continuous fractional quantification of cholesterol in high density lipoproteins and total cholesterol; and a quantification reagent kit to be used.

U.S. Pat. No. 5,705,515 to Fisher; Michael H. et al.; U.S. Pat. No. 6,043,253 to Brockunier; Linda et al.; U.S. Pat. No. 6,034,106 to Biftu; Tesfaye et al.; and U.S. Pat. No. 6,011,048 to Mathvink; Robert J. et al. (Merck) describes substituted sulfonamides, fused piperidine substituted arylsulfonamides; oxadiazole substituted benzenesulfonamides and thiazole substituted benzenesulfonamides, respectively, as $\beta_3$ adrenergic receptor agonists with very little $\beta_1$ and $\beta_2$ adrenergic receptor activity as such the compounds are capable of increasing lipolysis and energy expenditure in A cells. The compounds thus have potent activity in the treatment of Type II diabetes and obesity. The compounds can also be used to lower triglyceride levels and cholesterol levels or raise high density lipoprotein levels or to decrease gut motility. In addition, the compounds can be used to reduced neurogenic inflammation or as antidepressant agents. Compositions and methods for the use of the compounds in the treatment of diabetes and obesity and for lowering triglyceride levels and cholesterol levels or raising high density lipoprotein levels or for decreasing gut motility are also disclosed.

U.S. Pat. No. 5,773,304 to Hino discloses a method for quantitatively determining cholesterol in high density lipoproteins, in which, prior to the determination of cholesterol by an enzymatic method, a surfactant and a substance which forms a complex with lipoproteins other than high density lipoproteins are added to a sample containing lipoproteins. The method does not require any pretreatments such as centrifugal separation. With a simple operation, cholesterol in HDLs can be measured effectively. Also, this method can be adopted in a variety of automated analyzers, and thus is very useful in the field of clinical assays.

U.S. Pat. No. 5,707,822 to Fischettiet al. discloses methods and compositions for cloning and expression of serum opacity factor of Streptococcus pyogenes genes. The portion produced by the recombinant DNA techniques may be employed in qualitative and quantitative testing for high density lipoprotein, as a fibronectin binding factor and for the regulation of high density lipoprotein in a mammal. The gene may further be employed as a molecular probe for accurate identification of opacity factors from various strains of Streptococcus pyogenes.

U.S. Pat. No. 5,120,766 to Holloway et al. describes the use of 2-(phenoxypropanolamino)ethoxyphenoxyacetic acid derivatives or a pharmaceutically acceptable salt thereof, in lowering triglyceride and/or cholesterol levels and/or increasing high density lipoprotein levels. These compounds are used in treating hypertriglycerdaemia, hypercholesterolaemia, conditions of low HDL (high density lipoprotein) levels and atherosclerotic disease.

U.S. Pat. No. 6,193,967 to Morganelli discloses bispecific molecules which react both with an Fcγ receptor for immunoglobulin G (IgG) of human effector cells and with either human low density lipoprotein (LDL), or fragment thereof, or human high density lipoprotein (HDL), or a fragment thereof. The bispecific molecules bind to a Fcγ receptor without being blocked by the binding of IgG to the same receptor. The bispecific molecules having a binding specificity for human LDL are useful for targeting human effector cells for degradation of LDL in vivo. The bispecific molecules of the present invention which have a binding specificity for human HDL are useful for targeting human HDL to human effector cells such that the HDL takes up cholesterol from the effector cells. Also disclosed are methods of treating atherosclerosis using these bispecific molecules.

U.S. Pat. No. 6,162,607 to Miki et al. provides a method and a kit for measuring the amount of an objective constituent contained in a specific lipoprotein in a biological sample such as serum and plasma, specifically for measuring the amount of cholesterol contained in high density lipoprotein, which can be applicable to clinical tests.

U.S. Pat. No. 6,133,241 Bok et al. discloses a method for increasing the plasma high density lipoprotein (HDL) level in a mammal comprises administering a bioflavonoid or its derivative.

U.S. Pat. No. 6,090,836 to Adams et al. discloses acetylphenols which are useful as antiobesity and antidiabetic compounds. Compositions and methods for the use of the compounds in the treatment of diabetes and obesity and for lowering or modulating triglyceride levels and cholesterol levels or raising high density lipoprotein levels or for increasing gut motility or for treating atherosclerosis.

U.S. Pat. No. 5,939,435 to Babiak use of 2-substituted-1-acyl-1,2-dihydroquinoline derivatives to increase high density lipoprotein cholesterol (HDL-C) concentration and as therapeutic compositions for treating atherosclerotic conditions such as dyslipoproteinamias and coronary heart disease.

U.S. Pat. No. 5,932,536 to Wright et al. describe compositions and methods for neutralizing lipopolysaccharide, and treatment of gram-negative sepsis based therein. Accordingly, the invention is directed to a composition of homogeneous particles comprising phospholipids and a lipid exchange protein, such as phospholipid transfer protein or LPS binding protein. The lipid exchange protein is characterized by being capable of facilitating an exchange protein of lipopolysaccharide into the particles. In a specific embodiment, exemplified herein, the lipid particles are high density lipoprotein particles comprising apolipoprotein A-I (apo A-I), a phospholipid, and cholesterol or a lipid bilayer binding derivative thereof. In a specific example, the phospholipid is phosphatidylcholine (PC). In a specific example, the ratio of phosphatidylcholine:cholesterol:apolipoprotein A-I is approximately 80:4:1. The levels of LPS exchange protein activity in a sample from a patient provides a diagnostic, monitoring, or prognostic indicator for a subject with endotoxemia, gram-negative sepsis, or septic shock.

U.S. Pat. No. 4,215,993 to James L. Sanders describes a method for isolating high density lipoproteins from low density lipoproteins in human serum together with a quantitative determination of high density lipoprotein cholesterol. Precipitation of low density lipoproteins is accomplished by a precipitating reagent without the addition of metal ions into the sample. The precipitating reagent lowers the pH of the human serum approximately to the isoelectric point of the low density lipoproteins through the use of an organic buffer. The precipitating reagent also contains a polyanion and neutral polymer. The preferred composition of the precipitating reagent contains about 0.4% phosphotungstic acid by weight thereof, about 2.5% of polyethylene glycol by weight thereof and 2-i-morpholino) ethane sulfonic acid as the buffer present in a concentration of from about 0.2 molar to about 0.5 molar. According to the method provided, the precipitating reagent is added to the human serum sample thereby causing the low density lipoproteins to form a precipitate, leaving the high density lipoproteins in the resulting supernatant liquid. The supernatant is separated from the precipitate and a cholesterol assay reagent is added to the supernatant. The cholesterol assay reagent reacts with the high density lipoprotein to produce a compound that absorbs radiation at a specific wavelength. The amount of high density lipoprotein cholesterol present in the human serum sample is then determined by comparing the absorbance of a sample with the absorbance of a known standard.

U.S. Pat. No. 5,262,439 to Parthasarathy discloses analogs of probucol with increased water solubility in which one or both of the hydroxyl groups are replaced with ester groups that increase the water solubility of the compound. In one embodiment, the derivative is selected from the group consisting of a mono- or di-probucol ester of succinic acid, glutaric acid, adipic acid, seberic acid, sebacic acid, azelaic acid or maleic acid. In another embodiment, the probucol derivative is a mono- or di-ester in which the ester contains an alkyl or alkenyl group that contains a functionality selected from the group consisting of a carboxylic acid group, amine group, salt of an amine group, amide groups, amide groups and aldehyde groups.

WO 98/09773 filed by AtheroGenics, Inc. discloses that monoesters of probucol, and in particular, the monosuccinic acid ester of probucol, are effective in simultaneously reducing LDLc, and inhibiting the expression of VCAM-1. These compounds are useful as composite cardiovascular agents. Since the compounds exhibits three important vascular protecting activities simultaneously, the patient can take one drug instead of multiple drugs to achieve the desired therapeutic effect.

De Meglio et al., have described several ethers of symmetrical molecules for the treatment of hyperlipidemia. These molecules contain two phenyl rings attached to each other through a —S—C(CH$_3$)$_2$—S— bridge. In contrast to probucol, the phenyl groups do not have t-butyl as substituents. (De Meglio et al., *New Derivatives of Clofibrate and probucol: Preliminary Studies of Hypolipemic Activity*; Farmaco, Ed. Sci (1985), 40 (11), 833–44).

WO 00/26184 discloses a large genus of compounds with a general formula of phenyl-S-alkylene-S-phenyl, in which one or both phenyl rings can be substituted at any position. These compounds were disclosed as lubricants.

A series of French patents disclose that certain probucol ester derivatives are hypocholesterolemic and hypolipemic agents: Fr 2168137 (bis 4-hydroxyphenylthioalkane esters); Fr 2140771 (tetralinyl phenoxy alkanoic esters of probucol); Fr 2140769 (benzofuryloxyalkanoic acid derivatives of probucol); Fr 2134810 (bis-(3-alkyl-5-t-alkyl-4-thiazole-5-carboxy)phenylthio)alkanes; FR 2133024 (bis-(4-nicoinoyloxyphenythio)propanes; and Fr 2130975 (bis(4-(phenoxyalkanoyloxy)-phenylthio)alkanes).

U.S. Pat. No. 5,155,250 discloses that 2,6-dialkyl-4-silylphenols are antiatherosclerotic agents. The same compounds are disclosed as serum cholesterol lowering agents in PCT Publication No. WO 95/15760, published on Jun. 15, 1995. U.S. Pat. No. 5,608,095 discloses that alkylated-4-silyl-phenols inhibit the peroxidation of LDL, lower plasma cholesterol, and inhibit the expression of VCAM-1, and thus are useful in the treatment of atherosclerosis.

U.S. Pat. No. 5,783,600 discloses that dialkyl ethers lower Lp(a) and triglycerides and elevate HDL-cholesterol and are useful in the treatment of vascular diseases.

A series of European patent applications of Shionogi Seiyaku Kabushiki Kaisha disclose phenolic thioethers for use in treating arteriosclerosis. European Patent Application No. 348 203 discloses phenolic thioethers which inhibit the denaturation of LDL and the incorporation of LDL by macrophages. The compounds are useful as anti-arteriosclerosis agents. Hydroxamic acid derivatives of these compounds are disclosed in European Patent Application No. 405 788 and are useful for the treatment of arteriosclerosis, ulcer, inflammation and allergy. Carbamoyl and cyano derivatives of the phenolic thioethers are disclosed in U.S. Pat. No. 4,954,514 to Kita, et al.

U.S. Pat. No. 4,752,616 to Hall, et al., discloses arylthioalkylphenylcarboxylic acids for the treatment of thrombotic disease. The compounds disclosed are useful as platelet aggregation inhibitors for the treatment of coronary or cerebral thromboses and the inhibition of bronchoconstriction, among others.

A series of patents to Adir et Compagnie disclose substituted phenoxyisobutyric acids and esters useful as antioxidants and hypolipaemic agents. This series includes U.S. Pat. Nos. 5,206,247 and 5,627,205 to Regnier, et al. (which corresponds to European Patent Application No. 621 255) and European Patent Application No. 763 527.

WO 97/15546 to Nippon Shinyaku Co. Ltd. discloses carboxylic acid derivatives for the treatment of arterial sclerosis, ischemic heart diseases, cerebral infarction and post PTCA restenosis.

The Dow Chemical Company is the assignee of patents to hypolipidemic 2-(3,5-di-tert-butyl-4-hydroxyphenyl)thio carboxamides. For example, U.S. Pat. Nos. 4,029,812, 4,076,841 and 4,078,084 to Wagner, et al., disclose these compounds for reducing blood serum lipids, especially cholesterol and triglyceride levels.

WO 98/51662 filed by AtheroGenics, Inc. discloses therapeutic agents for the treatment of diseases, including cardiovascular diseases, which are mediated by VCAM-1, including compounds of formula I below. The PCT application also describes a method of inhibiting the peroxidation of LDL lipid, as well as lowering LDL lipids, in a patient in need thereof by administering an effective amount of the defined compound. The application does not address how to increase high density lipoprotein cholesterol levels, or how to improve the functionality of circulating high density lipoprotein.

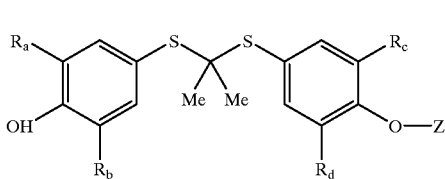

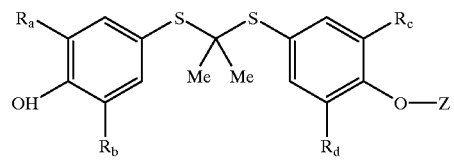

wherein

R$_a$, R$_b$, R$_d$, and R$_d$ are independently any group that does not otherwise adversely affect the desired properties of the molecule, including hydrogen, straight chained, branched, or cyclic alkyl which may be substituted, aryl, substituted aryl, heteroaryl, substituted heteroaryl, alkaryl, substituted alkaryl, aralkyl or substituted aralkyl; substituents on the R$_a$, R$_b$, R$_c$ and R$_d$ groups are selected from the group consisting of hydrogen, halogen, alkyl, nitro, amino, haloalkyl, alkylamino, dialkylamino, acyl, and acyloxy;

Z is selected from the group consisting of hydrogen, alkyl, substituted alkyl, alkenyl, substituted alkenyl, alkynyl, substituted alkynyl, aryl, aralkyl, alkaryl, heteroaryl, heteroaralkyl, a carbohydrate group, —(CH$_2$)—R$_e$, —C(O)—R$_g$, and —C(O)—(CH$_2$)$_n$—R$_h$, wherein (a) when each of R$_a$, R$_b$, R$_d$, and R$_d$ are t-butyl, Z cannot be hydrogen and (b) when each of R$_a$, R$_b$, R$_d$, and R$_d$ are t-butyl, Z cannot be the residue of succinic acid;

R$_e$ is selected from the group consisting of alkyl, substituted alkyl, alkenyl, substituted alkenyl, alkynyl, substituted alkynyl, alkoxy, substituted alkyloxy, alkoxyalkyl, substituted alkoxyalkyl, NH$_2$, NHR, NR$_2$, mono- or polyhydroxy-substituted alkyl, aryl, substituted aryl, heteroaryl, substituted heteroaryl, acyloxy, substituted acyloxy, COOH, COOR, —CH(OH)R$_k$, hydroxy, C(O)NH$_2$, C(O)NHR, C(O)NR$_2$;

R$_g$ is selected from the group consisting of alkyl, substituted alkyl, alkenyl, substituted alkenyl, alkynyl, substituted alkynyl, alkoxy, substituted alkyloxy, alkoxyalkyl, substituted alkoxyalkyl, NH$_2$, N-HR, NR$_2$, mono- or polyhydroxy-substituted alkyl, aryl, substituted aryl, heteroaryl, substituted heteroaryl;

R$_h$ is selected from the group consisting of alkyl substituted alkyl, alkenyl, substituted alkenyl, alkynyl, substituted alkynyl, alkoxy, substituted alkyloxy, alkoxyalkyl, substituted alkoxyalkyl, NH$_2$, NHR, NR$_2$, mono- or polyhydroxy-substituted alkyl, aryl, substituted aryl, heteroaryl, substituted heteroaryl, acyloxy, substituted acyloxy, COOH, COOR, —CH(OH)R$_k$, hydroxy, O-phosphate, C(O)NH$_2$, C(O)NHR, C(O)NR$_2$ and pharmaceutically acceptable salts thereof.

PCT/US01/09049, filed Mar. 21, 2001 by AtheroGenics, Inc., discloses a subclass of thioethers of formula (II) below that are useful in treating diseases mediated by VCAM-1, inflammatory disorders, cardiovascular diseases, occular diseases, autoimmune diseases, neurological diseases, cancer, hypercholesterolemia and/or hyperlipidemia. The application does not address how to increase high density lipoprotein cholesterol levels, or how to improve the functionality of circulating high density lipoprotein.

wherein a) R$_a$, R$_b$, R$_c$, and R$_d$ are independently any group that does not adversely affect the desired properties of the molecule, including hydrogen, alkyl, substituted alkyl, aryl, substituted aryl, heteroaryl, substituted heteroaryl, alkaryl, substituted alkaryl, aralkyl, or substituted aralkyl; and Z is (i) a substituted or unsubstituted carbohydrate, (ii) a substituted or unsubstituted alditol, (iii) C$_{1-10}$alkyl or substituted C$_{1-10}$alkyl, terminated by sulfonic acid, (iv) C$_{1-10}$alkyl or substituted C$_{1-10}$alkyl, terminated by phosphonic acid, (v) substituted or unsubstituted C$_{1-10}$alkyl-O—C(O)—C$_{1-10}$alkyl, (vi) straight chained polyhydroxylated C$_{3-10}$ alkyl; (vii) —(CR$_2$)$_{1-6}$—COOH, wherein R is independently hydrogen, halo, amino, or hydroxy, and wherein at least one of the R substituents is not hydrogen; or (viii) —(CR$_2$)$_{1-6}$—X, wherein X is aryl, heteroaryl, or heterocycle, and R is independently hydrogen, halo, amino, or hydroxy.

Since cardiovascular disease is the leading cause of death in North America and in other industrialized nations, there is a need to provide new therapies for its treatment, especially treatments that work through a mechanism different from the current drugs and can be used in conjunction with them.

It is an object of the present invention to provide new compounds, compositions and methods that are useful as HDLc elevating agents.

It is another object of the present invention to provide methods for identifying compounds that elevate plasma HDL cholesterol levels and improve the functionality of HDL.

It is another object of the present invention to provide methods for identifying compounds that increase selective uptake of cholesteryl esters.

It is another object of the present invention to provide a new method to improve the HDL/total cholesterol ratio by elevating HDLc levels.

It is another object of the present invention to provide an assay to assess the effectiveness of the new method to increase HDL cholesterol and HDL functionality.

It is another object of the present invention to provide assays to assess the effectiveness of the new method to increase HDL holoprotein levels by decreasing the internalization and degradation of HDL holoproteins.

It is still another object of the present invention to provide new compounds and compositions that increase the selective uptake of cholesteryl ester.

SUMMARY OF THE INVENTION

It has been discovered that certain selected ethers of probucol, and their pharmaceutically acceptable salts or prodrugs, are useful for increasing HDL cholesterol. These compounds may improve HDL functionality by increasing clearance of cholesteryl esters and increase HDL-particle affinity for hepatic cell surface receptors. In particular, effective compounds include those of the formulas:

Compound A

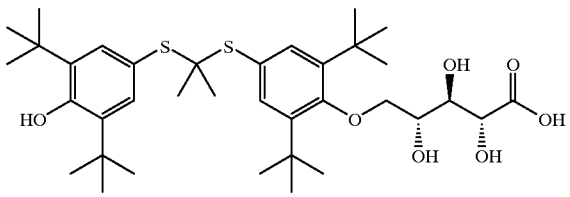

5-[4-[1-[[3,5-bis(1,1-dimethylethyl)-4-hydroxyphenyl]thio]-1-methylethyl]-thio-2,6-bis(1,1-dimethylethyl)phenoxy]-2(R),3(R),4(R)-trihydroxy-pentanoic Acid Compound B

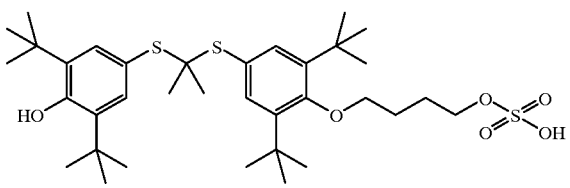

Sulfuric Acid, Mono(4-{2,6-di-tert-butyl-4-[1-(3,5-di-tert-butyl-4-hydroxy-phenyl-sulfany)-1-methylethylsulfanyl]-phenoxy}butyl)ester Compound C

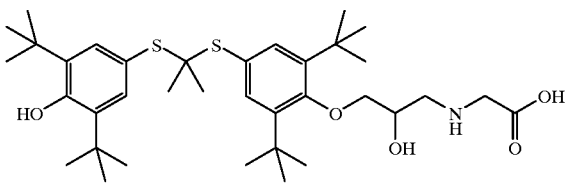

Glycine, N-[3-[4-[1-[[3,5-bis(1,1-dimethylethyl)-4-hydroxyphenyl]thio]-methylethyl]thio-2,6-bis(1,1-dimethylethyl)phenoxy]-2-hydroxypropyl]-

It has been discovered that these compounds significantly increase HDLc and improve HDL functionality without substantially increasing serum LDLc levels or decreasing apoAI protein synthesis. In other embodiments, compounds of the following formulas are provided.

Formula A

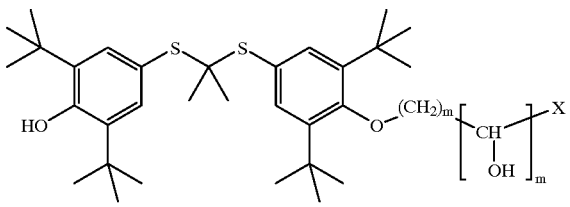

wherein
X=$CH_2C(O)_2R$, $C(O)_2R$, or $C(O)NR^1R^2$; n=1, 2, 3, 4, or 5; m=2, 3, 4, 5, 6, or 7; and R, $R^1$ and $R^2$ are independently hydrogen, alkyl, aryl, aralkyl, or alkaryl, which can be optionally substituted.

Formula B

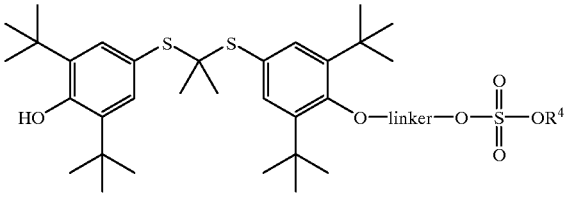

wherein
linker is alkyl or lower alkyl, alkenyl, alkynyl, heterocyclic, heteroaryl, aryl, aralkyl, heterocyclicalkyl, heteroarylalkyl, alkaryl, alkylheterocyclic, or alkylheteroaryl, which can be optionally substituted and $R^4$ is hydrogen, alkyl, alkenyl, alkynyl, heterocyclic, heteroaryl, aryl, aralkyl, heterocyclicalkyl, heteroarylalkyl, alkaryl, alkylheterocyclic, or alkylheteroaryl which can be optionally substituted.

Formula C

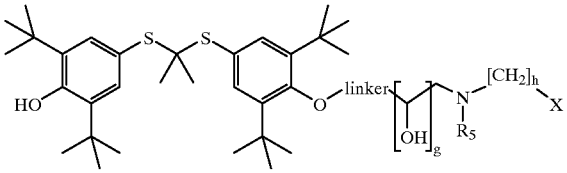

wherein
X=$CH_2C(O)_2R$, $C(O)_2R$, or $C(O)NR^1R^2$; h=1, 2, or 3; g=1, 2, 3, 4, 5, 6, or 7; and
R, $R^1$, $R^2$ and $R^5$ are independently hydrogen, alkyl, aryl, aralkyl, or alkaryl, which can be optionally substituted; linker is alkyl or lower alkyl.

Pharmaceutically acceptable compositions that include the above described compounds to increase HDLc and improve HDL functionality are also provided.

In another embodiment of the invention, a method for increasing circulating HDLc levels in a host in need thereof, including a human, is provided that includes administering an effective amount of one of the herein-described compounds or a physiologically acceptable salt thereof, or a pharmaceutically acceptable prodrug of said compound, optionally in a pharmaceutically acceptable carrier, that binds to a cholesterol-carrying lipoprotein (e.g., HDL) in a manner that increases the circulating plasma HDLc levels and improves HDL functionality, preferably by increasing the half-life of HDL, and increasing the selective uptake of cholesteryl esters, optionally, without substantially increasing the level of LDLc or decreasing apoAI synthesis.

In one embodiment, the HDLc increasing agent increases circulating HDLc by at least 20 percent in a treated host (for example, an animal, including a human), over the untreated serum level, and in a preferred embodiment, the compound increases circulating HDLc by at least 30, 40, 50, or 60 percent.

In another embodiment a method is provided for increasing circulating HDLc levels and improving HDL functionality by administering a compound or a pharmaceutically acceptable prodrug of said compound, or a physiologically acceptable salt thereof, optionally in a pharmaceutically acceptable carrier, to a host in need thereof including a human, is provided that includes administering an effective amount of a compound which binds to cholesterol-carrying lipoprotein (e.g., HDL) in a manner that increases the half-life of HDL by decreasing the internalization and degradation of HDL holoprotein particles and increases the selective uptake of cholesteryl ester (CE) by increasing the binding of cholesterol loaded HDL particles to cell surface receptors and increasing clearance of CE from CE loaded HDL particles, optionally, without substantially increasing the level of LDLc or decreasing apoAI synthesis.

In one embodiment, the HDL functionality increasing agent increases the measured half life of circulating apoAI-HDL by at least 20 percent in a treated host (for example, an animal, including a human), over the untreated serum level, and in a preferred embodiment, the compound increases the measured half life of circulating apoAI-HDL by at least 30, 40, 50, or 60 percent.

In another embodiment, the invention provides a new compound or a pharmaceutically acceptable prodrug of said compound, or a physiologically acceptable salt thereof, optionally in a pharmaceutically acceptable carrier, for increasing circulating HDLc levels and improving HDL functionality in a host by increasing the half-life of HDL and increasing the selective uptake of cholesteryl esters, optionally, without substantially increasing serum LDLc levels or decreasing apoAI protein synthesis.

In another embodiment, the invention provides a new compound or a pharmaceutically acceptable prodrug of said compound, or a physiologically acceptable salt thereof, optionally in a pharmaceutically acceptable carrier, for increasing HDL holoprotein levels in a host by decreasing the internalization, and optionally, the degradation of HDL holoproteins.

In another embodiment, assays are provided to identify compounds that increase circulating HDLc levels or increase the selective uptake of cholesteryl ester. It has been discovered that HDLc levels can be increased by administrating a compound that binds to cholesterol-carrying lipoprotein (e.g., HDL) in a manner that reduces hepatic and renal clearance of HDL holoproteins and additionally, increases the selective uptake of cholesteryl ester. Blocking the internalization of HDL holoprotein particles, and additionally increasing the binding of cholesteryl ester loaded HDL particles to cell surface proteins promotes the selective delivery of cholesterol to the liver for elimination. HDL holoprotein uptake is reduced causing an increase in the half-life of circulating apoAI-HDL. The increased half-life of HDL increases reverse transport of cholesterol because more HDL is available to deliver cholesteryl esters and facilitate their selective uptake.

According to this invention, one can determine whether a compound is an effective HDLc elevating compound using any of the methods described herein, including mixing the compound with cholesterol-containing lipoprotein in vivo or in vitro, isolating the complex, and determining whether the binding of the complex causes an increase in HDLc levels and improves HDL functionality by increasing the selective uptake of cholesteryl ester.

In another embodiment of the invention, an assay for determining whether a compound binds to a lipoprotein such as HDL in a manner which will increase circulating HDL holoprotein/apoAI-HDL levels is provided that includes assessing the ability of the compound to form a complex with the lipoprotein, e.g., HDL, determining whether the newly formed complex decreases the internalization and degradation of HDL holoprotein particles in a hepatic model, preferably hepatic cells.

In another embodiment of the invention, an assay for determining whether a compound binds to a lipoprotein such as HDL in a manner which will increase circulating HDLc levels and improve HDL functionality by increasing the selective uptake of cholesteryl esters is provided that includes assessing the ability of the compound to form a complex with the lipoprotein, e.g., HDL, determining whether the newly formed complex decreases the degradation of HDL holoprotein particles, and determining whether the newly formed complex enhances the delivery of cholesteryl ester from the HDL particle to a hepatic model, preferably hepatic cells, more preferably HepG2 cells, even more preferably a cell line stably transfected with the SR-BI gene.

In another embodiment of the invention, a method for selecting compounds that increase circulating HDLc levels is provided comprising, assessing the ability of the compound to form a complex with a lipoprotein, e.g., HDL, determining whether the complex causes an increase in serum apoAI-HDL, preferably by ELISA, optionally, without substantially increasing serum LDLc levels or decreasing apoAI protein synthesis.

As one nonlimiting example, the test compound can be fed to a host animal, for example a rabbit, together with a high-fat diet over time, preferably for six weeks, at a suitable dosage orally. The animals are then bled, preferably at six weeks, and plasma lipoproteins isolated, preferably by high speed centrifugation. The amount of test compound bound to each of the lipoproteins is then estimated. To determine if the bound test compound causes improved HDL functionality that would be therapeutically useful, a hepatic model, preferably hepatic cells, more preferably HepG2 cells, even more preferably a cell line stably transfected with the SR-BI gene, is first treated with the compound. Subsequently, the compound treated cells are again treated with the compound and labeled CE, preferably a radioactive isotope label, bound to HDL. After incubation, cells are washed, collected, and levels of labeled CE-HDL measured. An increase in labeled CE-HDL of cells treated with the compound compared to the amount of CE-HDL of cells not treated with the compound indicates a compound the increases the selective uptake of cholesterol or CE.

In another aspect of the invention, compounds that increase the levels of plasma HDL holoproteins can be selected using the following process. First, the compound is added to a hepatic model, preferably hepatic cells, more preferably HepG2 cells. Labeled apoAI-HDL, preferably a radioactive isotope label, more preferably $^{125}$I, in the presence or absence of compounds is then added to the cells. The trichloroacetic-precipitable labeled apoAI-HDL in the conditioned medium represents degraded labeled apoAI-HDL. After washing and detaching, cells are centrifuged. Labeled apoAI-HDL in the cellular fraction represents internalized HDL holoprotein; whereas, label in the supernatant represents cell surface bound apoAI-HDL that has been dissociated. Increased amounts of labeled HDL in cells treated with compounds versus cells not treated with compounds indicates increased degradation, internalization, or binding to the cell surface. Compounds are selected which decrease the amount of apoAI-HDL label in the cellular fraction of the cells contacted with a test compound compared to the amount of label in the cellular fraction of the cells not contacted with the test compound.

In another embodiment, the invention provides an assay to identify compounds which increase the delivery of cholesteryl ester to hepatic cells by contacting labeled cholesteryl ester, preferably a radiolabel, more preferably $^3$[H], with a test compound, contacting a hepatic model, preferably hepatic cells, more preferably HepG2 cells, even more preferably a cell line stably transfected with the SR-BI gene, with the combination of test compound and radiolabeled cholesteryl ester; separating the treated cells from the supernatant; washing the cells; measuring the amount of radiolabel associated with the washed cells; selecting the compound which causes a substantial increase in the amount of radiolabel associated with the washed cells treated with the test compound compared with the amount of radiolabel associated with cells not treated with the test compound.

In another embodiment, the invention provides an assay to identify compounds which increase the delivery of cholesteryl ester, and decrease HDL whole particle internalization and degradation. One can use a hepatic model, preferably hepatic cells, more preferably HepG2 cells, even more preferably a cell line stably transfected with the SR-BI gene. First, the test compound, labeled cholesteryl ester (preferably radiolabeled, such as with $^3[H]$), and labeled apoAI-HDL (preferably a radioactive isotope label such as preferably 125I), are added to a hepatic model, preferably hepatic cells, more preferably HepG2 cells, even more preferably a cell line stably transfected with the SR-BI gene. The treated cells are separated from the supernatant; the cells washed; and the amount of the two labels associated with the washed cells measured. Compounds are selected which cause a substantial increase in the amount of the labeled cholesteryl ester associated with cells in a hepatic model. In one embodiment, compounds increase cell-associated labeled cholesteryl ester by at least 25 percent over the untreated control, and in a preferred embodiment, the compound increases the labeled cholesteryl ester associated with cells in a hepatic model by at least 40, 50, 60, 75 or 100 percent.

In another embodiment, compounds are selected which cause a substantial decrease in HDL whole particle internalization and degradation by measuring the amount of labeled apoAI-HDL, preferably $^{125}I$-labeled apoAI-HDL, associated with cells in a hepatic model, preferably hepatic cells, more preferably HepG2 cells. In one embodiment, compounds decrease cell-internalized labeled apoAI-HDL by at least 20 percent over the untreated control, and in a preferred embodiment, the compound decreases the labeled apoAI-HDL associated with cells in a hepatic model by at least 30, 40, 50 or 60 percent.

In another embodiment, compounds are selected which cause a substantial decrease in HDL degradation by measuring the amount of labeled apoAI-HDL, preferably $^{125}I$-labeled apoAI-HDL, present in the cell supernatant after trichloroacetic acid precipitation. Preferably the cells are from a hepatic model, preferably hepatic cells, more preferably HepG2 cells. In one embodiment, compounds decrease the degradation of labeled apoAI-HDL by at least 20 percent over the untreated control, and in a preferred embodiment, the compound decreases the degradation of labeled apoAI-HDL in a hepatic model by at least 40, 50, 75 or 90 percent.

In another embodiment, the invention provides an assay to identify compounds which increase delivery of CE loaded HDL particles to a hepatic model, preferably hepatic cells, more preferably HepG2 cells, even more preferably a cell line stably transfected with the SR-BI gene, with the combination of test compound, labeled cholesteryl ester, preferably a radiolabel, more preferably $^3[H]$, separating the treated cells from the supernatant, washing the cells, measuring the amount of label associated with the washed cells, selecting the compound which causes a substantial increase in the amount of the label associated with the washed cells treated with the test compound compared with the amount of label associated with cells not treated with the test compound.

In another embodiment, the invention provides an assay to identify compounds that increase the selective uptake of cholesteryl esters by assessing the ability of the compound to form a complex with a lipoprotein, e.g., HDL, assessing the ability of the complex to bind to SR-BI protein, preferably purified SR-BI protein, and selecting the compound that increases whole particle HDL binding to SR-BI protein.

The finding that the above-identified compounds are useful to increase high density lipoprotein cholesterol levels, and to improve the functionality of circulating high density lipoprotein is quite unexpected in light of the fact that the following closely related compounds do not exhibit such activity, and in fact, act as LDL lowering agents. This dramatically illustrates that small changes in the molecule can significantly affect how the molecule modulates lipid levels, if at all.

Compound D

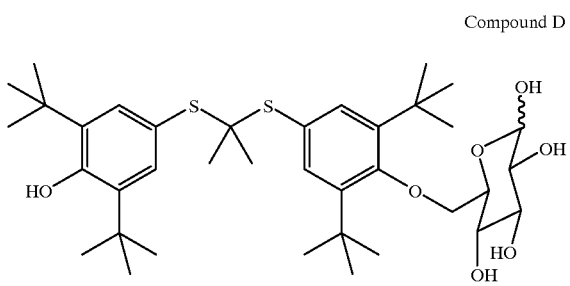

D-Glucopyranose, 6-O-[4-[1-[[3,5-bis(1,1-dimethylethyl)-4-hydroxyphenyl]thio]-1-methyl-ethyl]thio-2,6-bis(1,1-dimethylethyl)phenyl]

Compound E

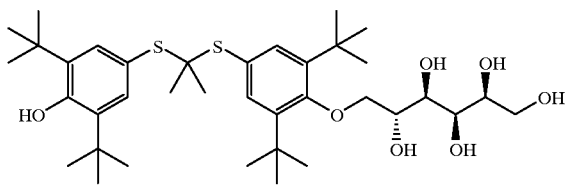

6-[4-[1-[[3,5-bis(1,1-dimethylethyl)-4-hydroxyphenyl]thio]-1-methylethyl]thio-2,6-bis(1,1-dimethylethyl)phenoxy]-2(S),3(R),4(R),5(R)-tetrahydroxyhexanol

BRIEF DESCRIPTION OF THE DRAWINGS

So that the matter in which the above-recited features, advantages, and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 5 shows the percent change in apoAI-HDL after treatment with 12.5 micromolar of the indicated compounds compared to control (absence of compounds) in the cell-based screen assay. FIG. 5 also shows the percent change of HDL cholesterol in hypercholesterolemic hamsters by the indicated compounds dosed at 150 mg/kg/d compared to untreated controls after two weeks of treatment.

DETAILED DESCRIPTION OF THE INVENTION

Figure 1:
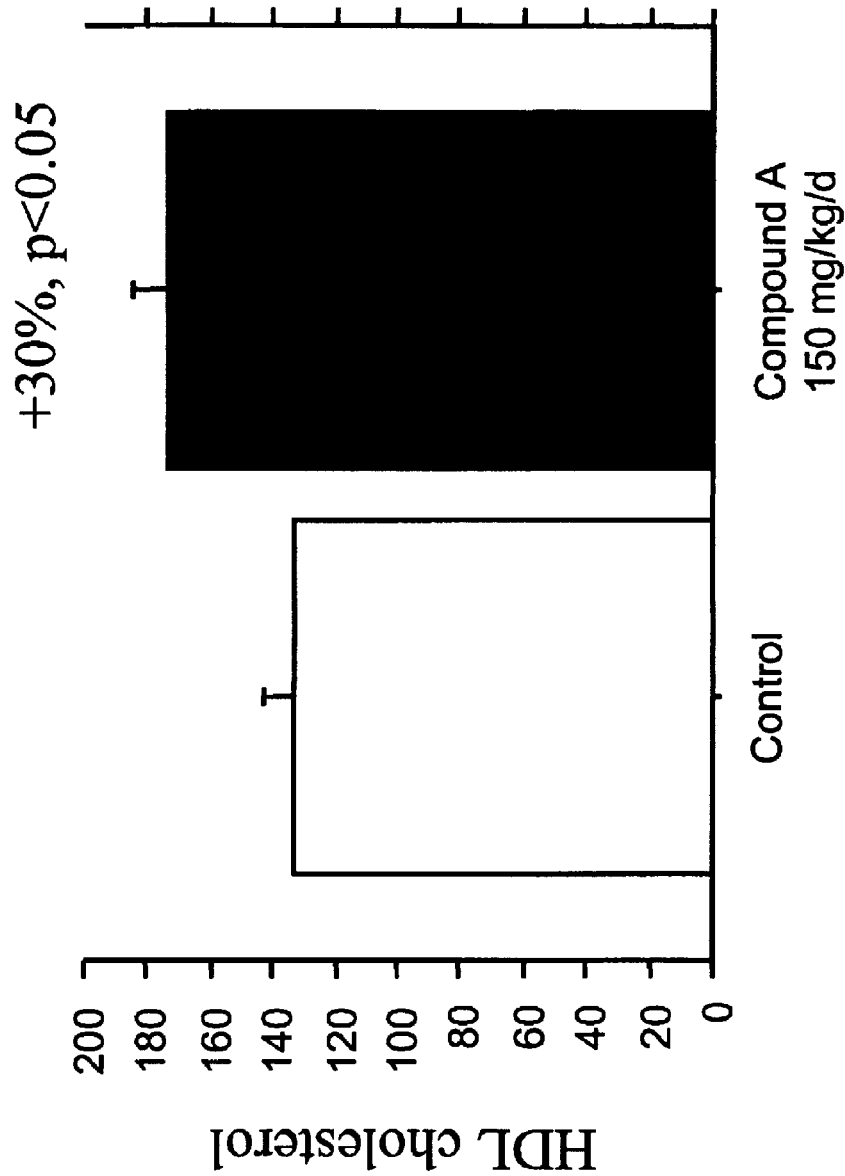
FIG. 1 is a bar graph demonstrating a 30% increase in HDL cholesterol levels in hypercholesterolemic hamsters treated with Compound A.

It has been discovered that certain selected ethers of probucol, and their pharmaceutically acceptable salts or prodrugs, are useful for increasing HDL cholesterol. These compounds may improve HDL functionality by increasing clearance of cholesteryl esters and increase HDL-particle affinity for hepatic cell surface receptors. In preferred embodiments, effective compounds include those of the formulas:

Compound A

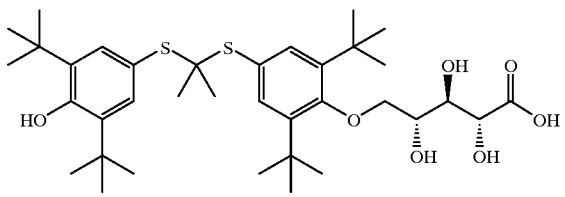

5-[4-[1-[[3,5-bis(1,1-dimethylethyl)-4-hydroxyphenyl] thio]-1-methylethyl]-thio-2,6-bis(1,1-dimethylethyl) phenoxy]-2(R),3(R),4(R)-trihydroxy-pentanoic Acid Compound B

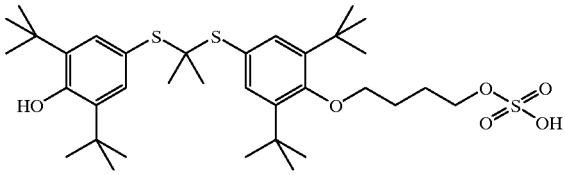

Sulfuric Acid, Mono (4-{2,6-di-tert-butyl-4-[1-(3,5-di-tert-butyl-4-hydroxy-phenyl-sulfany)-1-methylethylsulfanyl]-phenoxy}butyl)ester Compound C

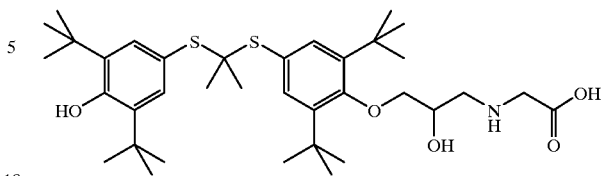

Glycine, N-[3-[4-[1-[[3,5-bis(1,1-dimethylethyl)-4-hydroxyphenyl]thio]-methylethyl]thio-2,6-bis(1,1-dimethylethyl)phenoxy]-2-hydroxypropyl]-

It has been discovered that these compounds significantly increase HDLc and improve HDL functionality without substantially increasing serum LDLc levels or decreasing apoAI protein synthesis.

It has been discovered that increased HDL cholesterol levels and improved HDL functionality can be obtained by administration of a compound that binds to cholesterol-carrying lipoprotein (e.g., HDL) in a manner that reduces hepatic clearance of HDL holoproteins, and additionally increases the selective uptake of cholesteryl ester. Blocking the internalization of HDL holoprotein particles, and additionally increasing the binding of cholesteryl ester loaded HDL particles to cell surface proteins promotes the selective delivery of cholesterol to the liver for elimination. HDL holoprotein uptake and degradation is reduced causing an increase in the half-life of circulating apoAI-HDL.

In one embodiment of the invention, a method for increasing circulating HDLc levels in a host in need thereof, including a human, is provided that includes administering an effective amount of a compound or a physiologically acceptable salt thereof, or a pharmaceutically acceptable prodrug of said compound, optionally in a pharmaceutically acceptable carrier, that binds to cholesterol-carrying lipoprotein (e.g., HDL) in a manner that increases the half-life of HDL holoproteins and increases the selective uptake of cholesteryl esters, optionally, without substantially increasing serum LDLc levels or decreasing apoAI protein synthesis.

In another embodiment of the invention, a method for increasing circulating HDLc levels in a host in need thereof, including a human, is provided that includes the administration of an effective amount of a compound, or a pharmaceutically acceptable prodrug of said compound, or a physiologically acceptable salt thereof, optionally in a pharmaceutically acceptable carrier, that binds to cholesterol-carrying lipoprotein (e.g., HDL) in a manner that increases the half-life of HDL by decreasing the internalization and degradation of HDL holoprotein particles and increases the selective uptake of cholesteryl esters optionally, without substantially increasing serum LDLc levels or decreasing apoAI protein synthesis.

In another embodiment of the invention, a method for increasing circulating apoAI-HDL and cholesterol levels in a host in need thereof, including a human, is provided that includes the administration of an effective amount of a compound, or a pharmaceutically acceptable prodrug of said compound, or a physiologically acceptable salt thereof, optionally in a pharmaceutically acceptable carrier, that binds to cholesterol-carrying lipoprotein (e.g., HDL) in a manner that increases the half-life of HDL by decreasing the internalization and degradation of HDL holoprotein and the selective uptake of cholesteryl esters by increasing the delivery of cholesteryl ester to hepatic cells from the HDL particle, preferably through increased cell surface binding of cholesterol loaded HDL particles, more preferably through increased binding of cholesterol loaded HDL particles to the surface of hepatic cells through cell surface receptors, even more preferably through increased binding of cholesterol loaded HDL particles to class B, type I and type II scavenger receptors.

According to the disclosed invention, one can determine whether a compound is an effective HDLc elevating compound by using any of the methods described herein, including mixing the compound with cholesterol-containing lipoprotein in vivo or in vitro, isolating the complex, and determining whether the binding of the complex increases circulating HDLc by decreasing HDL internalization and degradation or by increasing accumulation of apoAI-HDL.

If a host exhibiting a high plasma cholesterol level is given a compound which has been identified as a HDLc level elevating drug, and that host is nonresponsive to therapy, then the possibility exists that the host has a high cholesterol level because the host's apoAI protein is genetically diverse or altered in such a manner that it cannot not bind cholesteryl esters or is not present in sufficient quantities to reduce plasma cholesteryl esters in an effective manner. Therefore, the invention includes a method to assess whether a host has a variant of apoAI that when complexed in a lipoprotein, has a decreased ability to bind to a HDL receptor that includes monitoring the response of the host to a HDLc level enhancing drug, confirming that the patient has a lower than normal response to the drug, and then isolating and evaluating the host's apoAI protein for variations that result in decreased binding to the HDL receptor.

In another embodiment of the invention, a method for determining whether a compound will increase plasma HDLc levels is provided that includes assaying the ability of the compound to form a complex with a lipoprotein, preferably HDL, and then assessing whether the newly formed complex causes an increase in the half-life of apoAI-HDL by decreasing the internalization and degradation of HDL particles, optionally without substantially increasing serum LDLc levels or decreasing apoAI protein synthesis.

As one nonlimiting example of this embodiment, a method is provided comprising, a) contacting a test compound with whole HDL particles; b) contacting a hepatic model, preferably hepatic cells, more preferably HepG2 cells, even more preferably a cell line stably transfected with the SR-BI gene, with the combination of test compound with HDL particles; c) determining the level of apoAI-HDL accumulation, preferably using an ELISA assay; d) comparing the levels of apo-AI-HDL accumulation in a treated hepatic model with a hepatic model not contacted with the test compound; e) selecting the compound wherein there is a substantial increase in apo-AI-HDL accumulation, optionally without substantially decreasing apo-AI gene expression, apo-AI protein synthesis, or substantially increasing plasma LDLc levels.

As another nonlimiting example, a method is provided comprising, a) administering a test compound to an animal model over a period of time, preferably six weeks; b) monitoring the level of serum LDLc; c) monitoring the level of HDLc; d) assessing the reverse transport of cholesterol, preferably cholesteryl ester, e) comparing the levels of LDLc, HDLc and reverse transport of cholesterol in the animal model in which the compound was administered with the levels of LDLc, HDLc, and reverse transport in an animal model in which the compound was not administered; f) selecting the compound wherein there is a substantial increase in reverse transport of cholesterol, a substantial increase in HDLc levels, and a minimal increase in LDLc levels; g) selecting compounds which improve reverse cholesterol transport by assessing the the amount of cholesterol/cholesteryl ester present in the bile and/or stool in an animal model.

In another embodiment of the invention, a method for determining whether a compound will improve the functionality of circulating HDL is provided that includes assaying the ability of the compound to form a complex with a lipoprotein, preferably HDL, and then assessing whether the newly formed complex causes improved functionality of HDL through an increase in the selective uptake of CE, preferably through increased cell surface binding of cholesterol loaded HDL particles to hepatic cells, more preferably through increased binding of cholesterol loaded HDL particles on the surface of hepatic cells through cell surface receptors, even more preferably through increased binding of cholesteryl ester loaded HDL particles to class B, type I and type II scavenger receptors.

As one nonlimiting example of this embodiment, a method for determining whether a compound will increase circulating HDLc levels and increase the clearance of cholesteryl esters from the HDL particle is provided that includes: a) using a hepatic model, preferably hepatic cells, more preferably HepG2 cells, even more preferably a cell line stably transfected with the SR-BI gene; b) contacting the hepatic model with a cell surface receptor blocker, preferably an antibody against SR-BI/II scavenger receptors; c) contacting the cells from step (b) with a test compound; d) contacting the cells from step (c) with a labeled HDL, preferably $I^{125}$, loaded with a labeled cholesteryl ester, preferably with $^3[H]$; e) washing the cells from step (d); comparing the amount of label in cells from step (e) with the amount of label in control cells not treated with a cell surface receptor blocker; and f) selecting a compound wherein there is a decrease in the amount of labeled CE and labeled HDL in cells treated with a cell surface receptor blocker and test compound compared to the amount of label in cells not treated with a cell surface receptor blocker but treated with a test compound.

In another embodiment of the invention, a method for determining whether a compound will improve the functionality of circulating HDL is provided that includes assaying the ability of the compound to form a complex with a lipoprotein, preferably HDL, and then assessing whether the newly formed complex causes an increase in the half-life of apoAI-HDL and increases the selective uptake of cholesteryl esters.

As one nonlimiting example of this embodiment, the test compound can be fed to a host animal, for example a rabbit, together with a high-fat diet for six weeks at a suitable dosage orally. The animals are then bled, preferably at six weeks, and plasma lipoproteins isolated using high speed ultra-centrifugation. The amount of test compound bound to each of the lipoproteins is then estimated. To determine if the bound test compound causes an increase in the selective uptake of cholesterol that would be therapeutically useful, liver cells, preferably HepG2 cells, are first treated with the compound. Subsequently, the compound treated cells are again treated with the compound and labeled CE HDL, preferably a radioactive isotope label. After incubation, cells are washed, collected, and levels of labeled CE HDL measured. An increase in labeled CE HDL of cells treated with the compound compared to the amount of CE HDL of cells not treated with the compound indicates a compound the increases the selective uptake of cholesterol.

In another aspect of the invention, compounds that increase the levels of plasma HDLc can be selected by contacting a hepatic model, preferably hepatic cells, more preferably HepG2 cells with test compounds. Labeled apoAI-HDL, preferably a radioactive isotope label, more preferably $^{125}$I, in the presence or absence of compounds is then added to the cells. Label in the conditioned medium represents degraded labeled-HDL. After washing and detaching, cells are centrifuged. Label in the cellular fraction represents internalized HDL holoprotein; whereas, label in the supernatant represents cell surface bound apoAI-HDL that has been dissociated. Increased amounts of label in cells treated with compounds versus cells not treated with compounds indicates increased degradation, internalization, or binding of apoAI-HDL to the cell surface. Compounds are selected which decrease the amount of the apoAI-HDL label in the cellular fraction of the cells contacted with a test compound compared to the amount of label in the cellular fraction of the cells not contacted with the test compound.

In another aspect of the invention, compounds that increase circulating HDLc levels can be selected by: a) contacting a hepatic model, preferably hepatic cells, more preferably HepG2 cells, even more preferably a cell line stably transfected with the SR-BI gene, with a test compound b) assessing the ability of the compound to form a complex with a HDL particle; c) assessing the selective uptake of cholesteryl ester, preferably through cell surface receptors of the hepatic model, more preferably through SR-BI/II scavenger receptors; d) assessing the half-life of HDL particles; e) assessing the levels of serum LDLc; f) assessing the levels of apoAI protein synthesis; and g) selecting a the compound wherein, there is an increase over a control hepatic model, preferably HepG2 cells, not contacted with a test compound in the selective uptake of cholesteryl ester, optionally, with an increase in the half-life of apoAI-HDL, optionally without substantially increasing serum LDLc levels or decreasing apoAI protein synthesis.

In another embodiment, the invention provides an assay to identify compounds which increase the delivery of cholesteryl ester to hepatic cells by contacting a labeled cholesteryl ester, preferably a radiolabel, more preferably $^3$[H], loaded in HDL particles with a test compound, contacting a hepatic model, preferably hepatic cells, more preferably HepG2 cells, even more preferably a cell line stably transfected with the SR-BI gene, with the combination of test compound and radiolabeled cholesteryl ester; separating the treated cells from the supernatant; washing the cells; measuring the amount of radiolabel associated with the washed cells; selecting the compound which causes a substantial increase in the amount of radiolabel associated with the washed cells treated with the test compound compared with the amount of radiolabel associated with cells not treated with the test compound.

In another embodiment, the invention provides an assay to identify compounds which increase the delivery of cholesteryl ester to a hepatic model, preferably hepatic cells, more preferably HepG2 cells, even more preferably a cell line stably transfected with the SR-BI gene and decrease HDL whole particle internalization and degradation by contacting both labeled cholesteryl ester, preferably a radiolabel, more preferably $^3$[H], and labeled apoAI-HDL, preferably a radioactive isotope label, more preferably $^{125}$I, with a test compound, contacting a hepatic model, preferably hepatic cells, more preferably HepG2 cells, even more preferably a cell line stably transfected with the SR-BI gene, with the combination of test compound, labeled cholesteryl ester, and labeled apoAI-HDL; separating the treated cells from the supernatant; washing the cells; measuring the amount of the two labels associated with the washed cells; selecting the compound which causes a substantial increase in the amount of the labeled cholesteryl ester associated with cells and substantial decrease in the labeled apoAI-HDL associated with the washed cells treated with the test compound compared with the amount of labels associated with cells not treated with the test compound.

In another embodiment, the invention provides an assay to identify compounds which increase delivery of CE loaded HDL particles to a hepatic model, preferably hepatic cells, more preferably HepG2 cells, even more preferably a cell line stably transfected with the SR-BI gene, with the combination of test compound, labeled cholesteryl ester, preferably a radiolabel, more preferably $^3$[H], separating the treated cells from the supernatant, washing the cells, measuring the amount of label associated with the washed cells, selecting the compound which causes a substantial increase in the amount of the label associated with the washed cells treated with the test compound compared with the amount of label associated with cells not treated with the test compound.

In one nonlimity example, a method to select compounds that increase the delivery of cholesteryl ester to hepatic cells is provided comprising: a) contacting a hepatic model, preferably hepatic cells, more preferably HepG2 cells, even more preferably a cell line stably transfected with the SR-BI gene with a test compound in medium, preferably 1% RSA-DMEM, for 0–48 h., preferably 24 h., b) contacting the hepatic model with a mixture of test compound and $^3$[H]-CE HDL, preferably in a ratio of 1:2 (test compound to $^3$[H]-HDL); c) washing the hepatic model, d) measuring the amount of $^3$[H] associated with the cellular fraction, d) comparing the amount of $^3$[H] in cells treated with a test compound and cells not treated with test compound, and e) selecting the compound that substantially increases the amount of $^3$[H] associated with the cellular fraction compared to control cells not treated with test compounds.

In another embodiment, the invention provides an assay to identify compounds that increase the selective uptake of cholesteryl ester by assessing the ability of the compound to form a complex with a lipoprotein, e.g., HDL, assessing the ability of the complex to bind to SR-BI protein, preferably purified SR-BI protein, and selecting the compound that increases HDL whole particle binding to the SR-BI protein.

In another embodiment, the invention provides a new compound or a pharmaceutically acceptable prodrug of said compound, or a physiologically acceptable salt thereof, optionally in a pharmaceutically acceptable carrier, for increasing circulating HDLc levels in a host by increasing the half-life of apoAI-HDL and increasing the selective uptake of cholesteryl esters, optionally, without substantially increasing serum LDLc levels or decreasing apoAI protein synthesis.

In another embodiment, the invention provides a new compound or a pharmaceutically acceptable prodrug of said compound, or a physiologically acceptable salt thereof, optionally in a pharmaceutically acceptable carrier, for improving HDL functionality in a host by decreasing the internalization, and optionally, degradation of HDL holoproteins.

In summary, the invention includes the following embodiments:
(i) A method to assess whether a compound will increase circulating levels of HDLc and improve HDL functionality in a host including mixing the compound with cholesterol-containing lipoprotein in vivo or in vitro; isolating the complex, and determining whether the binding of the compound to the complex causes an increase in the functionality of HDL due to an increase in the selective uptake of cholesteryl ester optionally without substantially increasing the levels of LDLc and optionally without substantially decreasing the synthesis of apoAI;

(ii) A method to assess whether a compound will increase circulating levels of HDLc and improve HDL functionality in a host including mixing the compound with cholesterol-containing lipoprotein in vivo or in vitro; isolating the complex, and determining whether the binding of the compound to the complex causes an increase in circulating apoAI-HDL levels by decreasing the internalization and degradation of HDL holoprotein, and optionally, increasing the selective uptake of cholesterol, preferably cholesteryl esters;

(iii) A method to assess whether a compound will increase circulating levels of HDLc and improve HDL functionality in a host including mixing the compound with cholesterol-containing lipoproteins in vivo or in vitro, monitoring the half-life of apoAI-HDL, and selecting a drug that increases the half-life of apoAI-HDL.

(iv) A method to assess whether a compound will improve HDL functionality in a host including contacting a hepatic model, preferably hepatic cells, more preferably HepG2 cells with a test compound, monitoring the half-life of HDL, monitoring the accumulation of apoAI-HDL, and selecting a compound that increases circulating apoAI-HDL, optionally, without substantially increasing the levels of LDLc and optionally without substantially decreasing the synthesis of apoAI.

(v) A method to select compounds that increase the clearance of cholesteryl ester from whole HDL particles.

(vi) A method to select compounds that increase the binding of HDL particles to SR-BI protein.

(vii) A method for increasing circulating HDLc levels in a host, comprising administering to the host a compound that forms a complex with cholesterol-containing lipoprotein, e.g., HDL, or a pharmaceutically acceptable prodrug of said compound, or a physiologically acceptable salt thereof, optionally in a pharmaceutically acceptable carrier, that causes an increase in the half-life of HDL holoproteins and an increase in the selective uptake of cholesteryl ester;

(viii) A method for increasing the circulating levels of HDLc in a host comprising administering to the host a compound that forms a complex with cholesterol-containing lipoprotein, e.g., HDL, or a pharmaceutically acceptable prodrug of said compound, or a physiologically acceptable salt thereof, optionally in a pharmaceutically acceptable carrier and then assessing whether the newly formed complex causes an increase in the serum levels of HDLc and an increase in the selective uptake of cholesteryl esters optionally without substantially increasing the levels of LDLc; and (ix) Compounds and compositions, and pharmaceutically acceptable prodrugs and salts thereof, that increase circulating HDLc levels in a host without substantially increasing LDLc levels.

(x) Compounds and compositions, and pharmaceutically acceptable prodrugs and salts thereof, which increase circulating HDLc levels in a host and optionally increase the selective uptake of cholesteryl ester without substantially increasing LDLc levels.

(xi) Compounds and compositions, and pharmaceutically acceptable prodrugs and salts thereof, which improve the functionality of circulating HDL in a host by increasing the half-life of HDL.

(xii) Compounds and compositions, and pharmaceutically acceptable prodrugs and salts thereof, which increase circulating HDLc levels in a host, increasing the selective uptake of cholesteryl ester, and increasing the half-life of apoAI-HDL.

(xiii) Compounds and compositions, and pharmaceutically acceptable prodrugs and salts thereof, which increase circulating HDLc levels in a host by increasing the selective uptake of cholesteryl ester, increasing the half-life of apoAI-HDL without substantially increasing serum LDLc levels.

(xiv) A method for increasing circulating HDLc levels in a host comprising administering to a host a compound that forms a complex with cholesterol-containing lipoprotein, e.g., HDL, or a pharmaceutically acceptable prodrug of said compound, or a physiologically acceptable salt thereof, optionally in a pharmaceutically acceptable carrier, that increases the selective uptake of cholesteryl ester and optionally increases the half-life of apoAI-HDL optionally without substantially decreasing the synthesis of apoAI.

(xv) A method for increasing the levels of plasma HDLc in a host comprising administering to the host a compound that forms a complex with cholesterol-containing lipoprotein, e.g., HDL, or a pharmaceutically acceptable prodrug of said compound, or a physiologically acceptable salt thereof, optionally in a pharmaceutically acceptable carrier and then assessing whether the newly formed complex causes an increase in the serum levels of HDLc and improves HDL functionality by decreasing the internalization and degradation of HDL holoproteins or increasing the half life of apoAI-HDL optionally without substantially decreasing the synthesis of apo-AI.

I. Definitions

The term alkyl, as used herein, unless otherwise specified, refers to a saturated straight, branched, or cyclic, primary, secondary, or tertiary hydrocarbon, typically of $C_1$ to $C_{18}$, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of hydroxyl, carboxy, carboxamido, carboalkoxy, acyl, amino, alkylamino, arylamino, alkoxy, aryloxy, nitro, cyano, sulfonic acid, sulfate, phophonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference. Examples of substituted alkyl groups include trifluoromethyl and hydroxymethyl. The term alkyl includes terms "—(CH2)h-" "—(CH2)k-" or "—(CH2)n-" that represent a saturated alkylidene radical of straight chain configuration. The terms "n, j or k" can be any whole integer, including 0, 1, 2, 3, 4, 5, 6, 7, 8, 9, or 10. The moiety "—$(CH_2)_n$—" thus represents a bond (i.e., when n=0), methylene, 1,2-ethanediyl or 1,3-propanediyl, etc.

The term lower alkyl, as used herein, and unless otherwise specified, refers to a $C_1$ to $C_5$ saturated straight, branched, or if appropriate, a cyclic (for example, cyclopropyl) alkyl group. The lower alkyl group can be optionally substituted in the same manner as described above for the alkyl group.

The term "alkenyl," as referred to herein, and unless otherwise specified, refers to a straight, branched, or cyclic hydrocarbon of $C_2$ to $C_{10}$ with at least one double bond. The alkenyl group can be optionally substituted in the same manner as described above for the alkyl group.

The term "alkynyl," as referred to herein, and unless otherwise specified, refers to a $C_2$ to $C_{10}$ straight or branched hydrocarbon with at least one triple bond. The alkynyl group can be optionally substituted in the same manner as described above for the alkyl group.

The term aryl, as used herein, and unless otherwise specified, refers to phenyl, biphenyl, or naphthyl, and preferably phenyl. The aryl group can be optionally substituted with one or more moieties selected from the group consisting of hydroxyl, acyl, amino, halo, carboxy, carboxamido, carboalkoxy, alkylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term heteroaryl or heteroaromatic, as used herein, refers to an aromatic or unsaturated cyclic moiety that includes at least one sulfur, oxygen, nitrogen, or phosphorus in the aromatic ring. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, pyridazinyl, pyrazinyl, cinnolinyl, phthalazinyl, quinoxalinyl, xanthinyl, hypoxanthinyl, and pteridinyl. Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acycl groups such as acetyl and propionyl, methanesulfonyl, and p-toluenelsulfonyl. The heteroaryl or heteroaromatic group can be optionally substituted with one or more moieties selected from the group consisting of hydroxyl, acyl, amino, halo, alkylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term heterocyclic refers to a saturated nonaromatic cyclic group which may be substituted, and wherein there is at least one heteroatom, such as oxygen, sulfur, nitrogen, or phosphorus in the ring. The heterocyclic group can be substituted in the same manner as described above for the heteroaryl group.

The term aralkyl, as used herein, and unless otherwise specified, refers to an aryl group as defined above linked to the molecule through an alkyl group as defined above. The term alkaryl, as used herein, and unless otherwise specified, refers to an alkyl group as defined above linked to the molecule through an aryl group as defined above. The aralkyl or alkaryl group can be optionally substituted with one or more moieties selected from the group consisting of hydroxyl, carboxy, carboxamido, carboalkoxy, acyl, amino, halo, alkylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term halo, as used herein, specifically includes chloro, bromo, iodo, and fluoro.

The term alkoxy, as used herein, and unless otherwise specified, refers to a moiety of the structure —O-alkyl, wherein alkyl is as defined above.

The term acyl, as used herein, refers to a group of the formula C(O)R', wherein R' is an alkyl, aryl, alkaryl or aralkyl group, or substituted alkyl, aryl, aralkyl or alkaryl, wherein these groups are as defined above.

The term "amino acid" includes synthetic and naturally occurring amino acids, including but not limited to, for example, alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl.

The term pharmaceutically acceptable salts or complexes refers to salts or complexes that retain the desired biological activity of the compounds of the present invention and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —$NR^+A^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The term "lipoprotein" refers to proteins that transport lipids including chylomicrons, very low density lipoproteins (VLDL), low density lipoproteins (LDL), high density lipoproteins (HDL), LP(a), apolipoproteins (such as apoAI), or other proteins which complex with lipids.

The term "HDL holoprotein" refers to high density lipoprotein particles with apoAI as the major lipoprotein complexed with cholesterol, cholesteryl esters or other lipids.

The term "HDL functionality" refers to the ability of HDL to facilitate reverse cholesterol transport by the interaction of HDL with any protein or receptor involved in this process that will increase the half-life of apoAI-HDL in the plasma or increase the accumulation of secreted apoAI-HDL in an isolated cell system and/or increase the deliver of HDL cholesterol or cholesteryl esters to the liver for excretion or elimination through the interaction of HDL with the hepatic SRB receptor.

The term "host," as used herein, refers to any bone-containing animal, including, but not limited to humans, other mammals, canines, equines, felines, bovines (including chickens, turkeys, and other meat producing birds), cows, and bulls.

The term "cell surface receptor blocker" as used herein, refers to a compound, drug, protein including antibodies, or other ligand that binds reversibly or non-reversibly to the receptor preventing the natural ligand from binding to the receptor.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like. Such labels can be added to the proteins or cholesteryl esters of the present invention.

The term "prodrug," as used herein, refers to any compound which, upon administration to a host, is converted or metabolized to an active compound described herein.

II. Active Compounds

It has been discovered that these compounds significantly increase HDLc and improve HDL functionality without substantially increasing serum LDLc levels or decreasing apoAI protein synthesis. In one embodiment compounds of Formula A are provided.

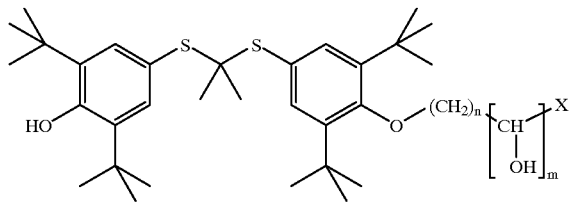

Formula A wherein
X=$CH_2C(O)_2R$, $C(O)_2R$, or $C(O)NR^1R^2$; n—1, 2, 3, 4, or 5; m=2, 3, 4, 5, 6, or 7; and R, $R^1$ and $R^2$ are independently hydrogen, alkyl, aryl, aralkyl, or alkaryl, which can be optionally substituted.

More particular embodiments of formula A are defined when:

X is $C(O)_2R$ (preferably COOH); n is 1, 2, or 3; or m is 3, 4, 5, or 6;

X is $C(O)_2R$ (preferably COOH); n is 1, 2, or 3; and m is 3, 4, 5, or 6;

X is $C(O)_2R$ (preferably COOH) and n is 1, 2, or 3;

X is $C(O)_2R$ (preferably COOH) and m is 3, 4, 5, or 6;

n is 1, 2, or 3 and m is 3, 4, 5, or 6;

X is $C(O)_2R$ (preferably COOH); n is 1, 2, or 3; and m is 3, 4, 5, or 6;

X is $C(O)_2R$, R is hydrogen or optionally substituted alkyl, n is 1, 2, or 3 and m is 3, 4, 5, or 6;

X is $C(O)_2R$ (preferably COOH), n is 1 and m is 3, 4, or 5; or

X is $C(O)_2R$ (preferably COOH), n is 1 and m is 3,

In another embodiment the invention provides compounds of Formula B:

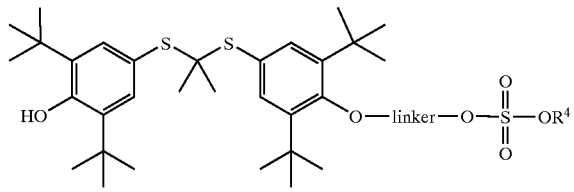

Formula B wherein
linker is alkyl or lower alkyl, alkenyl, alkynyl, heterocyclic, heteroaryl, aryl, aralkyl, heterocyclicalkyl, heteroarylalkyl, alkaryl, alkylheterocyclic, or alkylheteroaryl, which can be optionally substituted and $R^4$ is hydrogen, alkyl, alkenyl, alkynyl, heterocyclic, heteroaryl, aryl, aralkyl, heterocyclicalkyl, heteroarylalkyl, alkaryl, alkylheterocyclic, or alkylheteroaryl which can be optionally substituted.

More particular embodiments of formula B are defined when:

linker is —$(CH_2)_k$— and k is 2, 3, 4, 5, 6, 7, 8, 9, or 10;

linker is —$(CH_2)_k$— and k is 3, 4, 5, or 6;

$R^4$ is hydrogen;

linker is —$(CH_2)_k$, k is 2, 3, 4, 5, 6, 7, 8, 9, or 10, and $R^4$ is hydrogen;

linker is —$(CH_2)_k$—, k is 3, 4, 5, or 6, and $R^4$ is hydrogen;

linker is alkyl (optionally substituted); and linker is alkyl (optionally substituted), and $R^4$ is hydrogen.

In still another embodiment the invention provides compounds of Formula C:

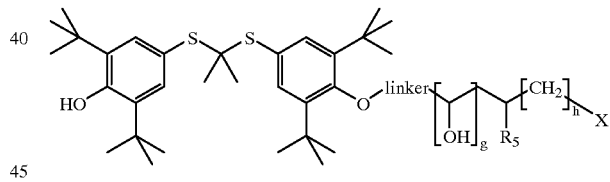

Formula C wherein
X=$CH_2C(O)_2R$, $C(O)_2R$, or $C(O)NR^1R^2$; h=1, 2, or 3; g=1, 2, 3, 4, 5, 6, or 7; and R,
$R^1$, $R^2$ and $R^5$ are independently hydrogen, alkyl, aryl, aralkyl, or alkaryl, which can be optionally substituted; linker is alkyl or lower alkyl.

More particular embodiments of formula C are defined when:

X is COOR (preferably COOH); $R^5$ is hydrogen; linker is —$(CH_2)_j$— and j is 1, 2, or 3 (preferably 1); h is 1; or g is 1;

X is COOR (preferably COOH); $R^5$ is hydrogen; linker is —$(CH_2)_j$— and j is 1, 2, or 3 (preferably 1); h is 1; and g is 1;

X is COOR (preferably COOH); and $R^5$ is hydrogen;

X is COOR (preferably COOH); $R^5$ is hydrogen; linker is —$(CH_2)_j$— and j is 1, 2, or 3 (preferably 1);

X is COOR (preferably COOH); $R^5$ is hydrogen; linker is —$(CH_2)_j$— and j is 1, 2, or 3 (preferably 1); and h is 1;

X is COOR (preferably COOH); R⁵ is hydrogen; linker is —(CH₂)ⱼ— and j is 1, 2, or 3 (preferably 1); and g is 1.

linker is —(CH₂)ⱼ— and j is 1, 2, or 3 (preferably 1); and h is 1;

linker is —(CH₂)ⱼ— and j is 1, 2, or 3 (preferably 1) and g is 1;

linker is —(CH₂)ⱼ— and j is 1, 2, or 3 preferably 1); h is 1; and g is 1;

X is COOR (preferably COOH); R⁵ is hydrogen; linker is alkyl (optionally substituted); h is 1; or g is 1;

X is COOR (preferably COOH); R⁵ is hydrogen; linker is alkyl (optionally substituted); h is 1; and g is 1;

X is COOR (preferably COOH); and R⁵ is hydrogen;

X is COOR (preferably COOH); R⁵ is hydrogen; linker is alkyl (optionally substituted);

X is COOR (preferably COOH); R⁵ is hydrogen; linker is alkyl (optionally substituted); and h is 1;

X is COOR (preferably COOH); R⁵ is hydrogen; linker is alkyl (optionally substituted); and g is 1.

linker is alkyl (optionally substituted); and h is 1;

linker is alkyl (optionally substituted) and g is 1; and linker is alkyl (optionally substituted); h is 1; and g is 1;

A preferred compound is defined by the following structure:

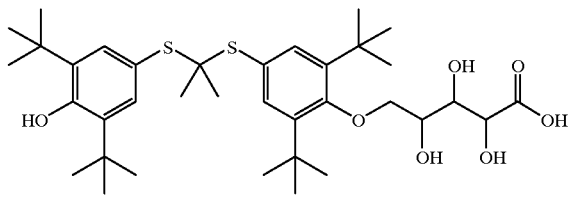

Particularly preferred compounds of the foregoing Formulas are compounds A, B, and C.

Pharmaceutical Compositions

Humans, equine, canine, bovine and other animals, and in particular, mammals, can be treated for any of the conditions described herein by administering to the patient an effective amount of one or more of the above-identified compounds or a pharmaceutically acceptable prodrug or salt thereof in a pharmaceutically acceptable carrier or diluent. Any appropriate route can be used to administer the active materials, for example, orally, parenterally, intravenously, intradermally, subcutaneously or topically.

As used herein, the term pharmaceutically acceptable salts or complexes refers to salts or complexes that retain the desired biological activity of the above-identified compounds and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with polyvalent metal cations such as zinc, calcium, bismuth, barium, magnesium, aluminum, copper, cobalt, nickel, cadmium, sodium, potassium, and the like, or with an organic cation formed from N,N-dibenzylethylene-diamine, D-glucosamine, ammonium, tetraethyl-ammonium, or ethylenediamine; or (c) combinations of (a) and (b); e.g., a zinc tannate salt or the like.

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.1 to 500 mg/kg, preferably 1 to 100 mg/kg per day. The effective dosage range of the pharmaceutically acceptable prodrugs can be calculated based on the weight of the parent compound to be delivered. If the derivative exhibits activity in itself, the effective dosage can be estimated as above using the weight of the derivative, or by other means known to those skilled in the art.

For systemic administration, the compound is conveniently administered in any suitable unit dosage form, including but not limited to one containing 1 to 3000 mg, preferably 5 to 500 mg of active ingredient per unit dosage form. An oral dosage of 25–250 mg is usually convenient. The active ingredient should be administered to achieve peak plasma concentrations of the active compound of about 0.1 to 100 mM, preferably about 1–10 mM. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable prodrugs or salts thereof can also be administered with other active materials that do not impair the desired action, or with materials that supplement the desired action, such as antibiotics, antifungals, anti-inflammatories, or antiviral compounds. The active compounds can be administered with lipid lowering agents such as probucol and nicotinic acid; platelet aggregation inhibitors such as aspirin; anti-thrombotic agents such as coumadin; calcium channel blockers such as varapamil, diltiazem, and nifedipine; angiotensin converting enzyme (ACE) inhibitors such as captopril and enalopril, and β-blockers such as propanalol, terbutalol, and labetalol. The compounds can also be administered in combination with nonsteroidal antiinflammatories such as ibuprofen, indomethacin, aspirin, fenoprofen, mefenamic acid, flufenamic acid, sulindac. The compound can also be administered with corticosteriods.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

Suitable vehicles or carriers for topical application are known, and include lotions, suspensions, ointments, creams, gels, tinctures, sprays, powders, pastes, slow-release transdermal patches, aerosols for asthma, and suppositories for application to rectal, vaginal, nasal or oral mucosa.

Thickening agents, emollients and stabilizers can be used to prepare topical compositions. Examples of thickening agents include petrolatum, beeswax, xanthan gum or polyethylene glycol, humectants such as sorbitol, emollients such as mineral oil, lanolin and its derivatives, or squalene. A number of solutions and ointments are commercially available.

Natural or artificial flavorings or sweeteners can be added to enhance the taste of topical preparations applied for local effect to mucosal surfaces. Inert dyes or colors can be added, particularly in the case of preparations designed for application to oral mucosal surfaces.

The active compounds can be prepared with carriers that protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylacetic acid. Many methods for the preparation of such formulations are patented or generally known to those skilled in the art.

If administered intravenously, preferred carriers are physiological saline or phosphate buffered saline (PBS).

The active compound can also be administered through a transdermal patch. Methods for preparing transdermal patches are known to those skilled in the art. For example, see Brown, L., and Langer, R., Transdermal Delivery of Drugs, Annual Review of Medicine, 39:221–229 (1988), incorporated herein by reference.

In another embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylacetic acid. Methods for preparation of such formulations will be apparent to those skilled in the art. The materials can also be obtained commercially from Alza Corporation and Nova Pharmaceuticals, Inc. Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

Stereoisomerism and Polymorphism

It is appreciated that compounds of the present invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms and how to determine antiproliferative activity using the standard tests described herein, or using other similar tests which are well known in the art. Examples of methods that can be used to obtain optical isomers of the compounds of the present invention include the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme iv) enzymatic asymmetric synthesis—a synthetic technique whereby at least one step of the synthesis uses an enzymatic reaction to obtain an enatiomerically pure or enriched synthetic precursor of the desired enantiomer;

v) chemical asymmetric synthesis—a synthetic technique whereby the desired enantiomer is synthesized from an achiral precursor under conditions that produce assymetry (i.e., chirality) in the product, which may be achieved using chrial catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatogaphy—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

III. Combination or Alternation Therapy

The compounds of the present invention can be combined with other biologically active compounds to achieve a number of potential objectives. For example, through dosage adjustment and medical monitoring, the individual dosages of the therapeutic compounds used in the combinations of the present invention will be lower than are typical for dosages of the therapeutic compounds when used in monotherapy. The dosage lowering will provide advantages including reduction of side effects of the individual therapeutic compounds when compared with the monotherapy. In addition, fewer side effects of the combination therapy compared with the monotherapies will lead to greater patient compliance with therapy regimens.

Another use of the present invention will be in combinations having complementary effects or complementary modes of action. Compounds of the present invention can be administered in combination with a drug that lowers cholesterol via a different biological pathway, to provide augmented results. For example, ileal bile acid transporter (IBAT) inhibitors frequently lower LDL lipoprotein but also lower HDL lipoprotein. In contrast, the compounds of the present invention typically raise HDL, A therapeutic combination of an IBAT inhibitor and a compound of the present invention will, when dosages are optimally adjusted, lower LDL yet maintain or raise HDL.

Compounds useful for combining with the compounds of the present invention encompass a wide range of therapeutic compounds. IBAT inhibitors, for example, are useful in the present invention, and are disclosed in patent application no. PCT/US95/10863, herein incorporated by reference. More IBAT inhibitors are described in PCT/US97/04076, herein incorporated by reference. Still further IBAT inhibitors useful in the present invention are described in U.S. application Ser. No. 08/816,065, herein incorporated by reference. More IBAT inhibitor compounds useful in the present invention are described in WO 98/40375, and WO 00/38725, herein incorporated by reference. Additional IBAT inhibitor compounds useful in the present invention are described in U.S. application Ser. No. 08/816,065, herein incorporated by reference.

In another aspect, the second cholesterol lowering agent is a statin. The combination of the HDLc enhancing drug with a statin creates a synergistic or augmented lowering of serum cholesterol, because statins lower cholesterol by a different mechanism, i.e., by inhibiting of 3-hydroxy-3-methylglutaryl coenzyme A (HMG CoA) reductase, a key enzyme in the cholesterol biosynthetic pathway. The statins decrease liver cholesterol biosynthesis, which increases the production of LDL receptors thereby decreasing plasma total and LDL cholesterol (Grundy, S. M. *New Engl. J. Med.* 319, 24 (1988); Endo, A. *J. Lipid Res.* 33, 1569 (1992)). Depending on the agent and the dose used, statins may decrease plasma triglyceride levels and may increase HDLc. Currently the statins on the market are lovastatin (Merck), simvastatin (Merck), pravastatin (Sankyo and Squibb) and fluvastatin (Sandoz). A fifth statin, atorvastatin (Parke-Davis/Pfizer), is the most recent entrant into the statin market. Any of these statins can be used in combination with the HDLc enhancing and HDL-functionality improving drug of the present invention.

The following list discloses these preferred statins and their preferred dosage ranges. The patent references are incorporated by reference as if fully set forth herein.

| | Trade name | Dosage range (mg/d) | Normal dose (mg/d) | Patent Reference |
|---|---|---|---|---|
| Fungal derivatives | | | | |
| lovastatin | Mevacor | 10–80 | 20–40 | 4,231,938 |
| pravastatin | Pravachol | 10–40 | 20–40 | 4,346,227 |
| simvastatin | Zocor | 5–40 | 5–10 | 4,739,073 |
| Synthetic compound | | | | |
| Fluvastatin | Lescol | 20–80 | 20–40 | 4,739,073 |

The following list describes the chemical formula of some preferred statins:

lovastatin: [1S[1a(R),3 alpha,7 beta,8 beta (2S,4S),8a beta]]-1,2,3,7,8,8a-hexahydro-3,7-dimethyl-8-[2-(tetrahydro-4- hydroxy-6-oxo-2H-pyran-2-yl)ethyl]-1-maphthalenyl-2-methylbutanoate pravastatin sodium: 1-Naphthalene-heptanoic acid, 1,2,6,7,8a-hexahydro-beta,delta,6-trihydroxy-2-methyl-8-(2-ethyl-1-oxybutoxy)-1-, monosodium salt [1S-[1 alpha (beta s, delta S),2 alpha,6 alpha,8 beta (R),8a alpha simvastatin: butanoic acid, 2,2-dimethyl-,1,2,3,7,8,8a-hexahydro-3,7-dimethyl-8-[2 tetrahydro-4-hydroxy-6-oxo-2H-pyran-2-yl)ethyl]-l-napthalenyl ester [1S-[1 alpha,3 alpha,7 beta,8 beta,(2S,4S),-8a beta sodium fluvastatin: [R,S-(E)]-(+/−)-7-[3(4-fluorophenyl)-1-(1-methylethyl)-1H-indol-2-yl]-3,5-dihydroxy-6-heptenoic acid, monosodium salt Other statins, and references from which their description can be derived, are listed below. The references are hereby incorporated by reference as if fully set for the herein:

| STATIN | REFERENCE |
|---|---|
| Atorvastatin | U.S. Pat. No. 5,273,995 |
| Cerivastatin (Baycol) | U.S. Pat. No. 5,177,080 |
| Mevastatin | U.S. Pat. No. 3,983,140 |
| Cerivastatin | U.S. Pat. No. 5,502,199 |
| Velostatin | U.S. Pat. No. 4,448,784 |
| Compactin | U.S. Pat. No. 4,804,770 |
| Dalvastatin | EP 738510 A2 |
| Fluindostatin | EP 363934 A1 |
| Dihydorcompactin | U.S. Pat. No. 4,450,171 |

Other statins include rivastatin, SDZ-63,370 (Sandoz), CI-981 (W-L). HR-780, L-645,164, CL-274,471, alpha-, beta-, and gamma-tocotrienol, (3R,5S,6E)-9,9-bis(4-fluorophenyl)-3,5-dihydroxy-8-(1-methyl-1H-tetrazol-5-yl)-6,8-nonadienoic acid, L-arginine salt, (S)-4-[[2-[4-(4-fluorophenyl)-5-methyl-2-(1-methylethyl)-6-phenyl-3-pyridinyl]ethenyl]-hydroxyphosphinyl]-3-hydroxybutanoic acid, disodium salt, BB-476, (British Biotechnology), dihydrocompactin, [4R-[4 alpha,6 beta (E)]]-6-[2-[5-(4-fluorophenyl)-3-(1-methylethyl)-1-(2-pyridinyl)-1H-pyrazol-4-yl]ethenyl]tetrahydro-4-hydroxy-2H-pyran-2-one, and 1H-pyrrole-1-heptanoic acid, 2-(4-fluorophenyl)-beta,delta-dihydroxy-5-(1-methylethyl)-3-phenyl-4-[(phenylamino)carbonyl]calcium salt[R-(R*,R*)].

However, the invention should not be considered to be limited to the foregoing statins. Naturally occurring statins are derivatives of fungi metabolites (ML-236B/compactin/monocalin K) isolated from *Pythium ultimum, Monacus ruber, Penicillium citrinum, Penicillium brevicompactum* and *Aspergillus terreus*, though as shown above they can be prepared synthetically as well. Statin derivatives are well known in the literature and can be prepared by methods disclosed in U.S. Pat. No. 4,397,786. Other methods are cited in The Peptides: Vol. 5, Analysis, Synthesis, Biology; Academic Press NY (1983); and by Bringmann et al. in Synlett (5), pp. 253–255 (1990).

Thus, the term statin as used herein includes any naturally occurring or synthetic peptide that inhibits 3-hydroxy-3-methylglutaryl coenzyme A (HMG CoA) reductase by competing with 3-hydroxy-3-methylglutaric acid (HMG) CoA for the substrate binding site on HMG-CoA reductase. Assays for determining whether a statin acts through this biological pathway are disclosed in U.S. Pat. No. 4,231,938, column 6, and WO 84/02131 on pages 30–33 (hereby incorporated by reference).

MTP inhibitor compounds useful in the combinations and methods of the present invention comprise a wide variety of structures and functionalities. Some of the MTP inhibitor compounds of particular interest for use in the present invention are disclosed in WO 00/38725, the disclosure from which is incorporated by reference. Descriptions of these therapeutic compounds can be found in *Science,* 282, 23 October 1998, pp. 751–754, herein incorporated by reference.

Cholesterol absorption antagonist compounds useful in the combinations and methods of the present invention comprise a wide variety of structures and functionalities. Some of the cholesterol absorption antagonist compounds of particular interest for use in the present invention are described in U.S. Pat. No. 5,767,115, herein incorporated by reference. Further cholesterol absorption antagonist compounds of particular interest for use in the present invention, and methods for making such cholesterol absorption antagonist compounds are described in U.S. Pat. No. 5,631,365, herein incorporated by reference.

A number of phytosterols suitable for the combination therapies of the present invention are described by Ling and Jones in "Dietary Phytosterols: A Review of Metabolism, Benefits and Side Effects," *Life Sciences,* 57 (3), 195–206 (1995). Without limitation, some phytosterols of particular use in the combination of the present invention are Clofibrate, Fenofibrate, Ciprofibrate, Bezafibrate, Gemfibrozil. The structures of the foregoing compounds can be found in WO 00/38725.

Phytosterols are also referred to generally by Nes (*Physiology and Biochemistry of Sterols,* American Oil Chemists' Society, Champaign, Ill., 1991, Table 7-2). Especially preferred among the phytosterols for use in the combinations of the present invention are saturated phytosterols or stanols. Additional stanols are also described by Nes (Id.) and are useful in the combination of the present invention. In the combination of the present invention, the phytosterol preferably comprises a stanol. In one preferred embodiment the stanol is campestanol. In another preferred embodiment the stanol is cholestanol. In another preferred embodiment the stanol is clionastanol. In another preferred embodiment the stanol is coprostanol. In another preferred embodiment the stanol is 22,23-dihydrobrassicastanol. In another embodiment the stanol is epicholestanol. In another preferred embodiment the stanol is fucostanol. In another preferred embodiment the stanol is stigmastanol.

In another embodiment the present invention encompasses a therapeutic combination of a compound of the present invention and another HDLc elevating agent. In one aspect, the second HDLc elevating agent can be a CETP inhibitor. Individual CETP inhibitor compounds useful in the present invention are separately described in WO 00/38725, the disclosure of which is herein incorporated by reference. Other individual CETP inhibitor compounds useful in the present invention are separately described in WO 99/14174, EP818448, WO 99/15504, WO 99/14215, WO 98/04528, and WO 00/17166, the disclosures of which are herein incorporated by reference. Other individual CETP inhibitor compounds useful in the present invention are separately described in WO 00/18724, WO 00/18723, and WO 00/18721, the disclosures of which are herein incorporated by reference. Other individual CETP inhibitor compounds useful in the present invention are separately described in WO 98/35937, the disclosure of which is herein incorporated by reference.

In another aspect, the second HDLc elevating agent can be a fibric acid derivative. Fibric acid derivatives useful in the methods and combinations of the present invention comprise a wide variety of structures and functionalities.

Preferred fibric acid derivatives for the present invention are described in Table 3. The therapeutic compounds of Table 3 can be used in the present invention in a variety of forms, including acid form, salt form, racemates, enantiomers, zwitterions, and tautomers. The individual U.S. patents referenced in Table 3 are each herein incorporated by reference.

TABLE 3

| Common Name | CAS Registry Number | U.S. Patent Reference for Compound Per Se |
|---|---|---|
| Clofibrate | 637-07-0 | 3,262,850 |
| Fenofibrate | 49562-28-9 | 4,058,552 |
| Ciprofibrate | 52214-84-3 | 3,948,973 |
| Bezafibrate | 41859-67-0 | 3,781,328 |
| Gemfibrozil | 25182-30-1 | 3,674,836 |

In another embodiment the present invention encompasses a therapeutic combination of a compound of the present invention and an antihypertensive agent. Hypertension is defined as persistently high blood pressure. Generally, adults are classified as being hypertensive when systolic blood pressure is persistently above 140 mmHg or when diastolic blood pressure is above 90 mmHg. Long-term risks for cardiovascular mortality increase in a direct relationship with persistent blood pressure. (E. Braunwald, *Heart Disease*, 5$^{th}$ ed., W. B. Saunders & Co., Philadelphia, 1997, pp. 807–823.) Blood pressure is a function of cardiac output and peripheral resistance of the vascular system and can be represented by the following equation:

$$BP = CO \times PR$$

wherein BP is blood pressure, CO is cardiac output, and PR is peripheral resistance. (Id., p. 816.) Factors affecting peripheral resistance include obesity and/or functional constriction. Factors affecting cardiac output include venous constriction. Functional constriction of the blood vessels can be caused y a variety of factors including thickening of blood vessel walls resulting in diminishment of the inside diameter of the vessels. Another factor which affects systolic blood pressure is rigidity of the aorta (Id., p. 811.)

Hypertension and atherosclerosis or other hyperlipidemic conditions often coexist in a patient. It is possible that certain hyperlipidemic conditions such as atherosclerosis can have a direct or indirect affect on hypertension. For example, atherosclerosis frequently results in diminishment of the inside diameter of blood vessels. Furthermore, atherosclerosis frequently results in increased rigidity of blood vessels, including the aorta. Both diminished inside diameter of blood vessels and rigidity of blood vessels are factors which contribute to hypertension.

Myocardial infarction is the necrosis of heart muscle cells resulting from oxygen deprivation and is usually cause by an obstruction of the supply of blood to the affected tissue. For example, hyperlipidemia or hypercholesterolemia can cause the formation of atherosclerotic plaques which can cause obstruction of blood flow and thereby cause myocardial infarction. (Id., pp. 1185–1187.) Another major risk factor for myocardial infarction is hypertension. (Id., p. 815.) In other words, hypertension and hyperlipidemic conditions such as atherosclerosis or hypercholesterolemia work in concert to cause myocardial infarction.

Coronary heart disease is another disease which is caused or aggravated by multiple factors including hyperlipidemic conditions and hypertension. Control of both hyperlipidemic conditions and hypertension are important to control symptoms or disease progression of coronary heart disease.

Angina pectoris is acute chest pain which is caused by decreased blood supply to the heart. Decreased blood supply to the heart is known as myocardial ischemia. Angina pectoris can be the result of, for example, stenosis of the aorta, pulmonary stenosis, and ventricular hypertrophy. Some antihypertensive agents, for example amlodipine, control angina pectoris by reducing peripheral resistance.

Some antihypertensive agents useful in the present invention are shown in Table 4, without limitation. A wide variety of chemical structures are useful as antihypertensive agents in the combinations of the present invention and the agents can operate by a variety of mechanisms. For example, useful antihypertensive agents can include, without limitation, an adrenergic blocker, a mixed alpha/beta adrenergic blocker, an alpha adrenergic blocker, a beta adrenergic blocker, an adrenergic stimulant, an angiotensin converting enzyme (ACE) inhibitor, an angiotensin II receptor antagonist, a calcium channel blocker, a diuretic, or a vasodilator. Additional hypertensive agents useful in the present invention are described by R. Scott in U.S. Patent Application No. 60/057,276 (priority document for PCT Patent Application No. WO 99/11260), herein incorporated by reference.

TABLE 4

| Antihypertensive Classification | Compound Name | Typical Dosage |
|---|---|---|
| adrenergic blocker | Phenoxybenzamine | 1–250 mg/day |
| adrenergic blocker | Guanadrel | 5–60 mg/day |
| adrenergic blocker | Guanethidine | |
| adrenergic blocker | Reserpine | |
| adrenergic blocker | Terazosin | 0.1–60 mg/day |
| adrenergic blocker | Prazosin | 0.5–75 mg/day |
| adrenergic blocker | Polythiazide | 0.25–10 mg/day |
| adrenergic stimulant | Methyldopa | 100–4000 mg/day |
| adrenergic stimulant | Methyldopate | 100–4000 mg/day |
| adrenergic stimulant | Clonidine | 0.1–2.5 mg/day |
| adrenergic stimulant | Chiorthalidone | 10–50 mg/day |
| adrenergic blocker | Guanfacine | 0.25–5 mg/day |
| adrenergic stimulant | Guanabenz | 2–40 mg/day |
| adrenergic stimulant | Trimethaphan | |
| alpha/beta adrenergic blocker | Carvedilol | 6–25 mg bid |
| alpha/beta adrenergic blocker | Labetalol | 10–500 mg/day |
| beta adrenergic blocker | Propranolol | 10–1000 mg/day |
| beta adrenergic blocker | Metoprolol | 10–500 mg/day |
| alpha adrenergic blocker | Doxazosin | 1–16 mg/day |
| alpha adrenergic blocker | Phentolamine | |
| angiotensin converting enzyme inhibitor | Quinapril | 1–250 mg/day |
| angiotensin converting enzyme inhibitor | perindopril erbumine | 1–25 mg/day |
| angiotensin converting enzyme inhibitor | Ramipril | 0.25–20 mg/day |
| angiotensin converting enzyme inhibitor | Captopril | 6–50 mg bid or tid |
| angiotensin converting enzyme inhibitor | Trandolapril | 0.25–25 mg/day |
| angiotensin converting enzyme inhibitor | Fosinopril | 2–80 mg/day |
| angiotensin converting enzyme inhibitor | Lisinopril | 1–80 mg/day |
| angiotensin converting enzyme inhibitor | Moexipril | 1–100 mg/day |
| angiotensin converting enzyme inhibitor | Enalapril | 2.5040 mg/day |
| angiotensin converting enzyme inhibitor | Benazepril | 10–80 mg/day |
| angiotensin II receptor antagonist | candesartan cilexetil | 2–32 mg/day |
| angiotensin II receptor antagonist | Inbesartan | |
| angiotensin II receptor antagonist | Losartan | 10–100 mg/day |

TABLE 4-continued

| Antihypertensive Classification | Compound Name | Typical Dosage | |
|---|---|---|---|
| angiotensin II receptor antagonist | Valsartan | 20–600 | mg/day |
| calcium channel blocker | Verapamil | 100–600 | mg/day |
| calcium channel blocker | Diltiazem | 150–500 | mg/day |
| calcium channel blocker | Nifedipine | 1–200 | mg/day |
| calcium channel blocker | Nimodipine | 5–500 | mg/day |
| calcium channel blocker | Delodipine | | |
| calcium channel blocker | Nicardipine | 1–20 | mg/hr i.v.; |
| | | 5–100 | mg/day oral |
| calcium channel blocker | Isradipine | | |
| calcium channel blocker | Amlodipine | 2–10 | mg/day |
| diuretic | Hydrochiorothiazide | 5–100 | mg/day |
| diuretic | Chiorothiazide | 250–2000 | mg bid or tid |
| diuretic | Furosemide | 5–1000 | mg/day |
| diuretic | Bumetanide | | |
| diuretic | ethacrynic acid | 20–400 | mg/day |
| diuretic | Amiloride | 1–20 | mg/day |
| Diuretic | Triameterene | | |
| Diuretic | Spironolactone | 5–1000 | mg/day |
| Diuretic | Eplerenone | 10–150 | mg/day |
| Vasodilator | Hydralazine | 5–300 | mg/day |
| Vasodilator | Minoxidil | 1–100 | mg/day |
| Vasodilator | Diazoxide | 1–3 | mg/kg |
| Vasodilator | Nitroprusside | | |

Additional calcium channel blockers which are useful in the combinations of the present invention include, without limitation, those shown in Table 5.

TABLE 5

| Compound Name | Reference |
|---|---|
| bepridil | U.S. Pat. No. 3,962,238 or U.S. Reissue No. 30,577 |
| clentiazem | U.S. Pat. No. 4,567,175 |
| diltiazem | U.S. Pat. No. 3,562,257 |
| fendiline | U.S. Pat. No. 3,262,977 |
| gallopamil | U.S. Pat. No. 3,261,859 |
| mibefradil | U.S. Pat. No. 4,808,605 |
| prenylamine | U.S. Pat. No. 3,152,173 |
| semotiadil | U.S. Pat. No. 4,786,635 |
| terodiline | U.S. Pat. No. 3,371,014 |
| verapamil | U.S. Pat. No. 3,261,859 |
| aranipine | U.S. Pat. No. 4,572,909 |
| bamidipine | U.S. Pat. No. 4,220,649 |
| benidipine | European Patent Application Publication No. 106,275 |
| cilnidipine | U.S. Pat. No. 4,672,068 |
| efonidipine | U.S. Pat. No. 4,885,284 |
| elgodipine | U.S. Pat. No. 4,962,592 |
| felodipine | U.S. Pat. No. 4,264,611 |
| isradipine | U.S. Pat. No. 4,466,972 |
| lacidipine | U.S. Pat. No. 4,801,599 |
| lercanidipine | U.S. Pat. No. 4,705,797 |
| manidipine | U.S. Pat. No. 4,892,875 |
| nicardipine | U.S. Pat. No. 3,985,758 |
| nifendipine | U.S. Pat. No. 3,485,847 |
| nilvadipine | U.S. Pat. No. 4,338,322 |
| nimodipine | U.S. Pat. No. 3,799,934 |
| nisoldipine | U.S. Pat. No. 4,154,839 |
| nitrendipine | U.S. Pat. No. 3,799,934 |
| cinnarizine | U.S. Pat. No. 2,882,271 |
| flunarizine | U.S. Pat. No. 3,773,939 |
| lidoflazine | U.S. Pat. No. 3,267,104 |
| lomerizine | U.S. Pat. No. 4,663,325 |
| Bencyclane | Hungarian Patent No. 151,865 |
| Etafenone | German Patent No. 1,265,758 |
| Perhexiline | British Patent No. 1,025,578 |

Additional ACE inhibitors which are useful in the combinations of the present invention include, without limitation, those shown in Table 6.

TABLE 6

| Compound Name | Reference |
|---|---|
| alacepril | U.S. Pat. No. 4,248,883 |
| benazepril | U.S. Pat. No. 4,410,520 |
| captopril | U.S. Pat. Nos. 4,046,889 and 4,105,776 |
| ceronapril | U.S. Pat. No. 4,452,790 |
| delapril | U.S. Pat. No. 4,385,051 |
| enalapril | U.S. Pat. No. 4,374,829 |
| fosinopril | U.S. Pat. No. 4,337,201 |
| imadapril | U.S. Pat. No. 4,508,727 |
| lisinopril | U.S. Pat. No. 4,555,502 |
| moveltopril | Belgian Patent No. 893,553 |
| perindopril | U.S. Pat. No. 4,508,729 |
| quinapril | U.S. Pat. No. 4,344,949 |
| ramipril | U.S. Pat. No. 4,587,258 |
| Spirapril | U.S. Pat. No. 4,470,972 |
| Temocapril | U.S. Pat. No. 4,699,905 |
| Trandolapril | U.S. Pat. No. 4,933,361 |

Additional beta adrenergic blockers which are useful in the combinations of the present invention include, without limitation, those shown in Table 7.

TABLE 7

| Compound Name | Reference |
|---|---|
| acebutolol | U.S. Pat. No. 3,857,952 |
| aiprenolol | Netherlands Patent Application No. 6,605,692 |
| amosulalol | U.S. Pat. No. 4,217,305 |
| arotinolol | U.S. Pat. No. 3,932,400 |
| atenolol | U.S. Pat. No. 3,663,607 or 3,836,671 |
| befunolol | U.S. Pat. No. 3,853,923 |
| betaxolol | U.S. Pat. No. 4,252,984 |
| bevantolol | U.S. Pat. No. 3,857,981 |
| bisoprolol | U.S. Pat. No. 4,171,370 |
| bopindolol | U.S. Pat. No. 4,340,641 |
| bucumolol | U.S. Pat. No. 3,663,570 |
| bufetolol | U.S. Pat. No. 3,723,476 |
| bufuralol | U.S. Pat. No. 3,929,836 |
| bunitrolol | U.S. Pat. Nos. 3,940,489 and 3,961,071 |
| buprandolol | U.S. Pat. No. 3,309,406 |
| butiridine hydrochloride | French Patent No. 1,390,056 |
| butofilolol | U.S. Pat. No. 4,252,825 |
| carazolol | German Patent No. 2,240,599 |
| carteolol | U.S. Pat. No. 3,910,924 |
| carvedilol | U.S. Pat. No. 4,503,067 |
| celiprolol | U.S. Pat. No. 4,034,009 |
| cetamolol | U.S. Pat. No. 4,059,622 |
| cloranolol | German Patent No. 2,213,044 |
| dilevalol | Clifton et al., Journal of Medicinal Chemistry, 1982 25, 670 |
| epanolol | European Patent Publication Application No. 41,491 |
| indenolol | U.S. Pat. No. 4,045,482 |
| labetalol | U.S. Pat. No. 4,012,444 |
| levobunolol | U.S. Pat. No. 4,463,176 |
| mepindolol | Seeman et al., Helv. Chim. Acta, 1971, 54, 241 |
| metipranolol | Czechoslovakian Patent Application No. 128,471 |
| metoprolol | U.S. Pat. No. 3,873,600 |
| moprolol | U.S. Pat. No. 3,501,769 |
| nadolol | U.S. Pat. No. 3,935,267 |
| nadoxolol | U.S. Pat. No. 3,819,702 |
| nebivalol | U.S. Pat. No. 4,654,362 |
| nipradilol | U.S. Pat. No. 4,394,382 |
| oxprenolol | British Patent No. 1,077,603 |
| perbutolol | U.S. Pat. No. 3,551,493 |

TABLE 7-continued

| Compound Name | Reference |
|---|---|
| pindolol | Swiss Patent Nos. 469,002 and 472,404 |
| practolol | U.S. Patent No. 3,408,387 |
| pronethalol | British Patent No. 909,357 |
| propranolol | U.S. Pat. Nos. 3,337,628 and 3,520,919 |
| sotalol | Uloth et al., Journal of Medicinal Chemistry, 1966, 9, 88 |
| sufinalol | German Patent No. 2,728,641 |
| talindol | U.S. Pat. Nos. 3,935,259 and 4,038,313 |
| tertatolol | U.S. Pat. No. 3,960,891 |
| tilisolol | U.S. Pat. No. 4,129,565 |
| timolol | U.S. Pat. No. 3,655,663 |
| toliprolol | U.S. Pat. No. 3,432,545 |
| Xibenolol | U.S. Pat. No. 4,018,824 |

Additional alpha adrenergic blockers which are useful in the combinations of the present invention include, without limitation, those shown in Table 8.

TABLE 8

| Compound Name | Reference |
|---|---|
| amosulalol | U.S. Pat. No. 4,217,307 |
| arotinolol | U.S. Pat. No. 3,932,400 |
| dapiprazole | U.S. Pat. No. 4,252,721 |
| doxazosin | U.S. Pat. No. 4,188,390 |
| fenspiride | U.S. Pat. No. 3,399,192 |
| indoramin | U.S. Pat. No. 3,527,761 |
| labetalol | U.S. Pat. No. 4,012,444 |
| naftopidil | U.S. Pat. No. 3,997,666 |
| nicergoline | U.S. Pat. No. 3,228,943 |
| prazosin | U.S. Pat. No. 3,511,836 |
| tamsulosin | U.S. Pat. No. 4,703,063 |
| Tolazoline | U.S. Pat. No. 2,161,938 |
| Trimazosin | U.S. Pat. No. 3,669,968 |
| Yohimbine | Raymond-Hamet, J. Pharm. Chim., 19, 209 (1934) |

Additional angiotensin II receptor antagonists which are useful in the combinations of the present invention include, without limitation, those shown in Table 9.

TABLE 9

| Compound Name | Reference |
|---|---|
| Candesartan | U.S. Pat. No. 5,196,444 |
| Eprosartan | U.S. Pat. No. 5,185,351 |
| Irbesartan | U.S. Pat. No. 5,270,317 |
| Losartan | U.S. Pat. No. 5,138,069 |
| Valsartan | U.S. Pat. No. 5,399,578 |

Additional vasodilators which are useful in the combinations of the present invention include, without limitation, those shown in Table 10.

TABLE 10

| Compound Name | Reference |
|---|---|
| aluminum nicotinate | U.S. Pat. No. 2,970,082 |
| amotriphene | U.S. Pat. No. 3,010,965 |
| bamethan | Corrigan et al., Journal of the American Chemical Society, 1945, 67, 1894 |
| bencyclane | Hungarian Patent No. 151,865 |
| bendazol | J. Chem. Soc., 1968, 2426 |
| benfurodil hemisuccinate | U.S. Pat. No. 3,355,463 |

TABLE 10-continued

| Compound Name | Reference |
|---|---|
| benziodarone | U.S. Pat. No. 3,012,042 |
| betahistine | Walter et al., Journal of the American Chemical Society, 1941, 63, 2771 |
| bradykinin | Hamburg et al., Arch. Biochem. Biophys., 1958, 76, 252 |
| brovincamine | U.S. Pat. No. 4,146,643 |
| bufeniode | U.S. Pat. No. 3,542,870 |
| buflomedil | U.S. Pat. No. 3,895,030 |
| butalamine | U.S. Pat. No. 3,338,899 |
| cetiedil | French Patent No. 1,460,571 |
| chioracizine | British Patent No. 740,932 |
| chromonar | U.S. Pat. No. 3,282,938 |
| ciclonicate | German Patent No. 1,910,481 |
| cinepazide | Belgian Patent No. 730,345 |
| cinnarizine | U.S. Pat. No. 2,882,271 |
| citicoline | Kennedy et al., Journal of the American Chemical Society, 1955, 77, 250 or synthesized as disclosed in Kennedy, Journal of Biological Chemistry, 1956, 222, 185 |
| clobenfliral | British Patent No. 1,160,925 |
| clonitrate | see Annalen, 1870, 155, 165 |
| cloricromen | U.S. Pat. No. 4,452,811 |
| cyclandelate | U.S. Pat. No. 2,707,193 |
| diisopropylamine dichloroacetate | Neutralization of dichloroacetic acid with diisopropyl amine |
| diisopropylamine dichloroacetate | British Patent No. 862,248 |
| dilazep | U.S. Pat. No. 3,532,685 |
| dipyridamole | British Patent No. 807,826 |
| droprenilamine | German Patent No. 2,521,113 |
| ebumamonine | Hermann et al., Journal of the American Chemical Society, 1979, 101, 1540 |
| efloxate | British Patent Nos. 803,372 and 824,547 |
| eledoisin | British Patent No. 984,810 |
| erythrityl | May be prepared by nitration of erythritol according to methods well-known to those skilled in the art. See e.g., Merck Index. |
| etafenone | German Patent No. 1,265,758 |
| fasudil | U.S. Pat. No. 4,678,783 |
| fendiline | U.S. Pat. No. 3,262,977 |
| fenoxedil | U.S. Pat. No. 3,818,021 or German Patent No. 1,964,712 |
| floredil | German Patent No. 2,020,464 |
| flunarizine | German Patent No. 1,929,330 or French Patent No. 2,014,487 |
| flunarizine | U.S. Pat. No. 3,773,939 |
| ganglefene | U.S.S.R. Patent No. 115,905 |
| hepronicate | U.S. Pat. No. 3,384,642 |
| hexestrol | U.S. Pat. No. 2,357,985 |
| hexobendine | U.S. Pat. No. 3,267,103 |
| ibudilast | U.S. Pat. No. 3,850,941 |
| ifenprodil | U.S. Pat. No. 3,509,164 |
| iloprost | U.S. Pat. No. 4,692,464 |
| inositol | Badgett et al., Journal of the American Chemical Society, 1947, 69, 2907 |
| isoxsuprine | U.S. Pat. No. 3,056,836 |
| itramin tosylate | Swedish Patent No. 168,308 |
| kallidin | Biochem. Biophys. Re&Commun., 1961, 6, 210 |
| kallikrein | German Patent No. 1,102,973 |
| khellin | Baxter et al., Journal of the Chemical Society, 1949, 5 30 |
| lidofiazine | U.S. Pat. No. 3,267,104 |
| lomerizine | U.S. Pat. No. 4,663,325 |
| mannitol hexanitrate | May be prepared by the nitration of mannitol according to methods well-known to those skilled in the art |
| medibazine | U.S. Pat. No. 3,119,826 |
| moxisylyte | German Patent No. 905,738 |
| nafronyl | U.S. Pat. No. 3,334,096 |
| nicametate | Blicke & Jenner, J. Am. Chem. Soc., 64, 1722 (1942) |

TABLE 10-continued

| Compound Name | Reference |
| --- | --- |
| nicergoline | U.S. Pat. No. 3,228,943 |
| nicofuranose | Swiss Patent No. 366,523 |
| nimodipine | U.S. Pat. No. 3,799,934 |
| nitroglycerin | Sobrero, Ann., 64, 398 (1847) |
| nylidrin | U.S. Pat. Nos. 2,661,372 and 2,661,373 |
| papaverine | Goldberg, Chem. Prod. Chem. News, 1954, 17, 371 |
| pentaerythritol tetranitrate | U.S. Pat. No. 2,370,437 |
| pentifylline | German Patent No. 860,217 |
| pentoxifylline | U.S. Pat. No. 3,422,107 |
| pentrinitrol | German Patent No. 63 8,422-3 |
| perhexilline | British Patent No. 1,025,578 |
| pimefylline | U.S. Pat. No. 3,350,400 |
| piribedil | U.S. Pat. No. 3,299,067 |
| prenylamine | U.S. Pat. No. 3,152,173 |
| propatyl nitrate | French Patent No. 1,103,113 |
| prostaglandin El | May be prepared by any of the methods referenced in the Merck Index, Twelfth Edition, Budaved, Ed., New Jersey, 1996, p. 1353 |
| suloctidil | German Patent No. 2,334,404 |
| tinofedrine | U.S. Pat. No. 3,563,997 |
| tolazoline | U.S. Pat. No. 2,161,938 |
| trapidil | East German Patent No. 55,956 |
| tricromyl | U.S. Pat. No. 2,769,015 |
| trimetazidine | U.S. Pat. No. 3,262,852 |
| trolnitrate phosphate | French Patent No. 984,523 or German Patent No. 830,955 |
| vincamine | U.S. Pat. No. 3,770,724 |
| vinpocetine | U.S. Pat. No. 4,035,750 |
| Viquidil | U.S. Pat. No. 2,500,444 |
| Visnadine | U.S. Pat. Nos. 2,816,118 and 2,980,699 |
| xantbinol niacinate | German Patent No. 1,102,750 or Korbonits et al., Acta. Pharm. Hung., 1968, 38, 98 |

Additional diuretics which are useful in the combinations of the present invention include, without limitation, those shown in Table 11.

TABLE 11

| Compound Name | Reference |
| --- | --- |
| Acetazolamide | U.S. Pat. No. 2,980,676 |
| Aithiazide | British Patent No. 902,658 |
| Amanozine | Austrian Patent No. 168,063 |
| Ambuside | U.S. Pat. No. 3,188,329 |
| Amiloride | Belgian Patent No. 639,386 |
| Arbutin | Tschb&habln, Annalen, 1930, 479, 303 |
| Azosemide | U.S. Pat. No. 3,665,002 |
| Bendroflumethiazide | U.S. Pat. No. 3,265,573 |
| Benzthiazide | McManus et al., 136th Am. Soc. Meeting (Atlantic City, September 1959). Abstract of Papers, pp 13–0 |
| benzylhydro-chlorothiazide | U.S. Pat. No. 3,108,097 |
| Bumetanide | U.S. Pat. No. 3,634,583 |
| Butazolamide | British Patent No. 769,757 |
| Buthiazide | British Patent Nos. 861,367 and 885,078 |
| Chloraminophenamide | U.S. Pat. Nos. 2,809,194, 2,965,655 and 2,965,656 |
| Chlorazanil | Austrian Patent No. 168,063 |
| Chlorothiazide | U.S. Pat. Nos. 2,809,194 and 2,937,169 |
| Chlorthalidone | U.S. Pat. No. 3,055,904 |
| Clofenamide | Olivier, Rec. Tray. Chim., 1918, 37, 307 |
| Clopamide | U.S. Pat. No. 3,459,756 |
| Clorexolone | U.S. Pat. No. 3,183,243 |
| Cyclopenthiazide | Belgian Patent No. 587,225 |

TABLE 11-continued

| Compound Name | Reference |
| --- | --- |
| Cyclothiazide | Whitehead et al., Journal of Organic Chemistry, 1961, 26, 2814 |
| Disulfamide | British Patent No. 851,287 |
| Epithiazide | U.S. Pat. No. 3,009,911 |
| ethacrynic acid | U.S. Pat. No. 3,255,241 |
| Ethiazide | British Patent No. 861,367 |
| Ethoxolamide | British Patent No. 795,174 |
| Etozolin | U.S. Pat. No. 3,072,653 |
| Fenquizone | U.S. Pat. No. 3,870,720 |
| Furosemide | U.S. Pat. No. 3,058,882 |
| Hydracarbazine | British Patent No. 856,409 |
| Hydrochlorothiazide | U.S. Pat. No. 3,164,588 |
| Hydroflumethiazide | U.S. Pat. No. 3,254,076 |
| Indapamide | U.S. Pat. No. 3,565,911 |
| Isosorbide | U.S. Pat. No. 3,160,641 |
| Mannitol | U.S. Pat. No. 2,642,462; or 2,749,371; or 2,759,024 |
| Mefruside | U.S. Pat. No. 3,356,692 |
| Methazolamide | U.S. Pat. No. 2,783,241 |
| Methyclothiazide | Close et al., Journal of the American Chemical Society, 1960, 82, 1132 |
| Meticrane | French Patent Nos. M2790 and 1,365,504 |
| Metochalcone | Freudenberg et al., Ber., 1957, 90, 957 |
| Metolazone | U.S. Pat. No. 3,360,518 |
| Muzolimine | U.S. Pat. No. 4,018,890 |
| Paraflutizide | Belgian Patent No. 620,829 |
| Perhexiline | British Patent No. 1,025,578 |
| Piretanide | U.S. Pat. No. 4,010,273 |
| Polythiazide | U.S. Pat. No. 3,009,911 |
| Quinethazone | U.S. Pat. No. 2,976,289 |
| Teclothiazide | Close et al., Journal of the American Chemical Society, 1960, 82, 1132 |
| Ticrynafen | U.S. Pat. No. 3,758,506 |
| Torasemide | U.S. Pat. No. 4,018,929 |
| Triamterene | U.S. Pat. No. 3,081,230 |
| Trichlormethiazide | deStevens et al., Experientia, 1960, 16,113 |
| Tripamide | Japanese Patent No. 73 05,585 |
| Urea | Can be purchased from commercial sources |
| Xipamide | U.S. Pat. No. 3,567,777 |

IV. Assays

The invention includes assays to determine (i) whether a compound will improve plasma HDL functionality by causing an increase in the selective uptake of cholesterol; (ii) whether a compound will increase plasma HDL cholesterol and holoprotein/apoAI levels by causing an increase in the half-life of apoAI-HDL; (iii) whether a compound which increases plasma HDL levels increases the binding of HDL loaded with cholesterol and CE to hepatic cell surface receptors; and (iv) whether a compound that increases plasma HDL levels by increasing the accumulation of apoAI-HDL levels.

The assays described herein can be performed using cell lines stably transfected with SR-BI or hepatic cells including HepG2 cells. Primary cultures of hepatic cells may also be used in these assays. Cholesteryl esters and HDL particles can be labeled with radioactive isotopes including $^{125}I$ or $^{3}H$ or any other label including enzymatic or fluorescent labels for determining the uptake and binding of cholesteryl ester or whole HDL particles.

V. Materials and Method

Animal and Diets

Male Golden Syrian hamsters weighing 110–120 g were obtained from Charles River Laboratories (Wilmington, Mass.). Hamsters were housed individually with wood chip bedding and soft nesting material with lights on a 6 A.M. and off at 6 p.m. Upon arrival the hamsters were acclimated for three days on standard rodent chow and water (Purina rodent chow 5001) ad libitum. Prior to dosing, the hamsters were made hypercholesterolemic by feeding them a powdered diet supplemented with 0.5% cholesterol and 10% coconut oil (Harlan Teklad diet #97235) for one week. Water was added to the powdered chow to form a paste and the chow paste rolled into balls with each animal receiving 20 g of chow paste per day in stainless steel bowls. Chow intake was recorded daily. Body weights were recorded after one week and at the end of the end of the study. Hamsters were distributed into treatment groups after the one-week pretreatment period such that each group had similar average body weights.

Compound A homogenized in methylcellulose/Tween-20 using a polytron PT2100 homogenizer (Brinkman) before adding it to the high cholesterol chow paste and administered as an admixture at the same time each morning for two weeks. At the end of the treatment period the hamsters were fasted in the late afternoon on the day prior to blood collection. Fasting was achieved by transferring the hamsters to clean cages and removing chow stored in cheek pouches. Hamsters were anesthetized with ketamine/rompun solution. When unresponsive to toe pinch and still respiring, blood was collected via cardiac puncture from which plasma was separated and frozen at −80° C.

Lipid Analysis

Lipoproteins were isolated from whole plasma by Fast Phase Liquid Chromatography (FPLC). Cholesterol and triglyceride concentrations in the different lipoprotein fractions were determined by enzymatic methods using a CX-5 chemical analyzer and standard Beckman reagents.

Statistical Analysis

A Dunnetts test was used to compare the experimental and control groups. P<0.05 was considered significant.

Lipoproteins

HDL3 (d=1.12–1.21 g/mL) and lipoprotein-deficient plasma (d>1.21 g/ml fraction) were isolated by sequential flotation ultracentrifugation from fresh plasma of normolipidemic human blood donors, and were obtained from the core laboratory of the Biochemistry Department of the Allegheny University of the Health Sciences (Lund-Katz, S., and Phillips, M. C. (1986) *Biochemistry* 25, 1562–1568). HDL3, kept in high KBr salt was extensively dialyzed against 150 mM NaCl, prior to use, and appeared as a single band on agarose gel electrophoresis.

Cell Culture

HepG2 cells were obtained from the American Type Culture Collection (Rockville, Md.). Fetal bovine serum (FBS) was purchased from Gibco Laboratories. Cells were cultured in minimum essential medium (MEM) containing 10% FBS, and 100 μg/mL of streptomycin, 100 unit/mL of penicillin, and 4 mM of glutamine (Gibco/BRL). Cells were grown for 2 days till they are 80% confluent in 6-well, or 12-well plates before studies. In all cases medium was changed every other day.

Quantification of Secreted Human apoAI by Enzyme-linked Immunoassay (ELISA)

To measure apoAI, 96-well microtiter plates were coated with a 1:1000 diluted mixture of three monoclonal antibodies against human apoAI (A05, A17, and A44) for 2 h and incubated in succession with HDL3 (0 to 15 ng/well), sheep polyclonal anti-apoAI serum (Boehringer Mannheim), alkaline phosphatase-labeled rabbit anti-sheep (Cappel), and p-nitrophenyl phosphate (1 mg/mL in 10 mmol/L ethanolamine, 0.5 mmol/L MgCl$_2$, pH 9.5), for 2, 1 and 1 h respectively at 37° C. The plates were washed three times between different incubations. The absorbance at 405 nm was determined by using a Bio-Rad model 550 microplate reader (Bio-Rad).

Preparation and Uptake of $^3$[H]cholesteryl Hexadecyl Ether-Labeled HDL $^3$[H]cholesteryl Hexadecyl Ether-labeled HDL was prepared as described by Rodrigueza et al. (Rodrigueza W. V. et al. (1999) *J. Biol. Chem.* 274:20344–20350). 40 μCi of $^3$[H] hexadecyl ether (40–60 Ci/mmol, NEN life Sciences Products) were incubated with 5 mg of HDL3 and 240 mg of heat-inactivated lipoprotein-deficient plasma, 0.01% aprotinin in a polypropylene tube sealed with nitrogen gas for 40 h at 37° C. according to the method of Terpstra et al. $^3$[H]-CE enriched HDL was re-isolated by flotation ultracentrifugation and dialyzed against phosphate-buffered saline (PBS). To perform CE uptake studies, HepG2 cells, seeded in 6 or 12 well plates were grown for 2 days till 80% confluent and, then treated with compounds in 1% RSA-DMEM medium for 24 h. The next day, cells were treated with 12.5 μM compounds and 50 μg/mL of $^3$[H]-CE HDL for 3.5 h at 37° C. After incubation, cells were washed 4 times with PBS/BSA and 2 times with PBS, followed by addition of 0.1 N NAOH. Cells were collected, and radioactivity was measured in counts per minute and expressed as percent of 3[H]-CE delivered to cells.

VI. Syntheses

The active compounds of the formula (I) can be prepared by any known methods, including those described in WO 98/51662 and PCT/US01/09049. General procedures for preparing compounds of formula (I) wherein Z represents the ether group are set forth in General Procedures A wherein all substituents, unless otherwise indicated, are previously defined.

General Procedure A

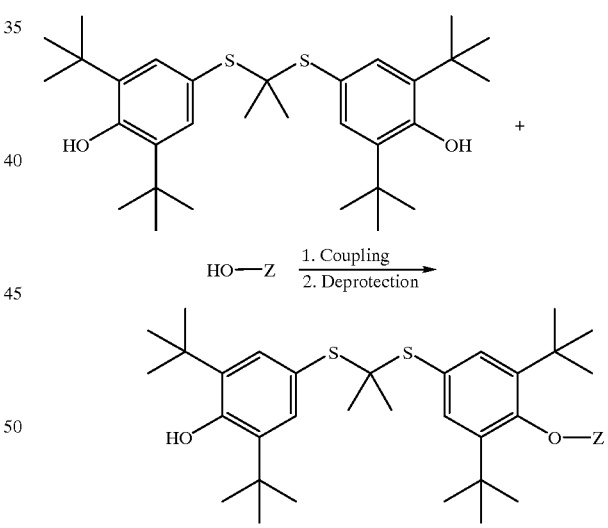

Compounds of the present invention can be readily prepared by someone skilled in the art of organic synthesis using a standard ether coupling procedure known as the Mitsunobu reaction (Hughes, D. L., "The Mitsunobu reaction" in Organic Reactions (N.Y.) (1992), Vol. 42, pp 335–656). For example, to a solution of probucol in a suitable aprotic solvent such as tetrahydrofuran (THF) are added triphenylphosphine, diethyl azodicarboxylate, and an appropriate alcohol moiety optionally containing the additional substituents described above for Z. The resultant mixture is stirred under nitrogen at reflux for 2 to 8 hours and then evaporated. Chromatography on silica gel gives the desired ether product. Alternatively, one skilled in the art can replace the triphenyl-phosphine reagent with other suitable phosphine reagents, including but not limited to tributylphosphine and polymer-supported triphenylphosphine. One may also use dimethyl azidodicarboxylated in place of diethyl azidodicarboxylate. Since Z may also contain one or more alcohol, amine, or carboxylate substituents that may participate in the reaction, one normally skilled in the art may choose to protect these substituent groups prior to the reaction using standard procedures known in the literature ("Protective Groups in Organic Synthesis" (3rd Edition) Edited by T. W. Greene, P. G. M. Wuts, John Wiley and Sons, Inc., New York, N.Y.). Compounds of the present invention include the resulting protected intermediates. Alternatively, one skilled in the art can selectively remove these protecting groups using well established and known procedures to give the desired ether products containing one or more deprotected alcohol, amine, or carboxylate substituents in Z. Preferably, the alcohol group used to make the ether in Z above is a primary alcohol.

The chemical reactions described above are generally disclosed in terms of their broadest applications to the preparation of the compounds of the present invention. Occasionally, the reactions may not be applicable as described to each compound included within the disclosed scope. The compounds for which this occurs will be readily recognized by those skilled in the art. In all such cases, either the reactions can successfully performed by conventional modifications recognized by those skilled in the art, e.g., by appropriate protection and deprotection of interfering groups, by changing to alternative conventional solvents or reagents, by routine modification of reaction conditions and the like, or other conventional reactions will be applicable to the preparation of the corresponding compounds of the present invention. In all preparative methods, all starting materials are known or readily prepared from known starting materials.

EXAMPLES

Example 1

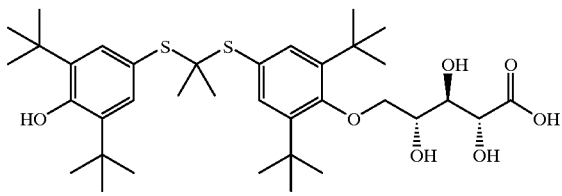

5-[4-[1-[(3,5-bis(1,1-dimethylethyl)-4-hydroxyphenyl)thiol]-1-methylethyl]thio-2,6-bis(1,1-dimethylethyl)phenoxy]-2(R),3(R),4(R)-trihydroxypentanoic Acid ("Compound A")

A mixture of D-(+)-ribonic gamma-lactone (5.2 g), triethyl orthoformate (148.2 g) and THF (100 mL) was stirred at reflux for 16 h. The mixture was evaporated under reduced pressure to give a solid residue (6.9 g), 1 g of which was mixed with probucol (3 g), triphenylphosphine (1.54 g) and diethyl azodicarboxylate (0.93 mL) in THF (40 mL). The mixture was stirred at reflux for 3 h and then evaporated to a residue. Chromatography on silica gel gave the expected ether product (0.46 g), 0.45 g of which was suspended in a mixture of acetic acid and water (8:2, 10 mL). The suspension was stirred at room temperature for 3 h. Methanol was added until the mixture became a solution. The mixture was then stirred at reflux overnight. Most of the solvent was removed at reduced pressure and the remainder was neutralized with 1 N sodium hydroxide solution. It was extracted with dichloromethane, dried over sodium sulfate and evaporated to give a white solid (0.41 g), 0.2 g of which was dissolved in THF (5 mL). Sodium hydroxide solution (1 N, 4 equivalents) was added and the mixture was stirred at room temperature for 3 h. the solvent was removed at reduced pressure and the residue was taken up with dichloromethane. The solution was dried over sodium sulfate and evaporated. Chromatography on silica gel (15% to 25% methanol in dichloromethane) gave 0.2 g of the desired 5-[4-[1-[(3,5-bis(1,1-dimethylethyl)-4-hydroxyphenyl)thio]-1-methylethyl]thio-2,6-bis-(1,1-di-methylethyl)phenoxy]-2(R),3(R),4(R)-trihydroxypentanoic acid product as a white solid.

Example 2

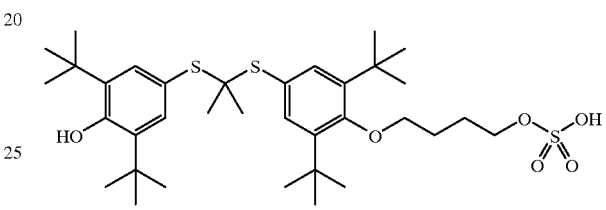

Sulfuric Acid, Mono-(4-{2,6-di-tert-butyl-4-[1-(3,5-di-tert-butyl-4-hydroxy-phenyl-sulfanyl)-1-methylethylsulfanyl]-phenoxy}-butyl)ester ("Compound "B"")

EX-2A)

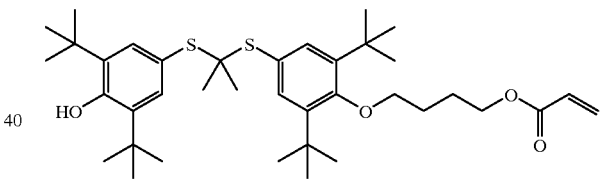

A solution of probucol (2.58 g, 5 mmol) in 50 mL of THF was treated with 4-hydroxy-butyl acrylate (1 mL, 10 mmol), triphenylphosphine (2.62 g, 10 mmol), and diethyl azodicarboxylate (1.57 mL, 10 mmol). The resulting mixture was stirred under reflux for 3 days then cooled to room temperature. The solvent was evaporated. Purification of the crude material by column chromatography (SiO$_2$; 4:1 hexanes-CH$_2$Cl$_2$) gave the desired ether product as a brown oil (0.92 g).

EX-2B)

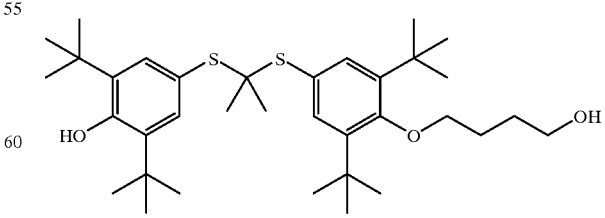

The product from EX-2A (0.82 g) was suspended in methanol (20 mL) then treated with potassium carbonate (0.5 g). The resulting mixture was stirred at room temperature overnight. The mixture was then poured into water (50 mL), and extraction was performed with Et$_2$O (2×50 mL). The combined ether extracts were dried, and solvent was removed by evaporation. Purification using column chromatography (SiO$_2$; 4:1 hexanes-EtOAc) gave the desired γ-hydroxybutyl ether as a colorless oil which eventually solidified (0.52 g).

EX-2) The product from EX-2B (90 mg; 0.15 mmol) was dissolved in DMF (2 mL). The solution was treated with SO$_3$.Et$_3$N (42 mg; 0.3 mmol), then stirred at room temperature overnight. The mixture was poured into ether (100 mL) and washed with water (3×100 mL). The organic phase was dried; solvent was removed by evaporation to give the desired sulfuric acid, mono-(4-{2,6-di-tert-butyl-4-[1-(3,5-di-tert-butyl-4-hydroxyphenyl-sulfanyl)-1-methyl-ethylsulfanyl]-phenoxy}-butyl) ester ("Compound "B"product as a white foam (37 mg).

Example 3

Related compounds can be prepared by one skilled in the art using methods previously described in WO 98/51662 and U.S. Pat. No. 6,147,250, as summarized below in Example Table 1.

Hamsters were anesthetized with ketamine/rompun solution. When unresponsive to toe pinch and still respiring, blood was collected via cardiac puncture from which plasma was separated and frozen at −80° C.

FIG. 1 shows that Compound A elevated HDL cholesterol in hypercholesterolemic hamsters by 30% compared to untreated controls after two weeks of treatment at a dose of 150 mg/kg/d. LDL cholesterol was not affected. Lipid profiles were obtained according to the method published by Lee, A. and coworkers (W. Innis-Whitehouse, X. Li, V. Brown and N. Lee., *J. Lipid Res.* 39, 679 (1998)). The compound was well-tolerated and all animals gained weight.

Example 5

The effect of Compound A on apoAI-HDL elevation was measured using a cell-based screen assay. The hepatic model, HepG2 cells, was used to observe the accumulation of apoAI as a result of secretion and/or uptake of apoAI; both processes taking place in the liver. HepG2 cells were treated with compounds for 24 hours or 48 hours in DMEM containing 1% RSA. apoAI accumulation was measured by ELISA as described in Materials and Methods. Different concentrations of compounds were used, and 12.5 μM was

TABLE 1

Example

| Structure | Designation | Example No. |
|---|---|---|
| [Structure of Compound C: bis-tert-butyl phenol thioether with O-CH$_2$-CH(OH)-CH$_2$-NH-CO$_2$H side chain] | Compound C | 3a |
| [Structure of Compound D: bis-tert-butyl phenol thioether with O-linked pyranose sugar] | Compound D | 3b |
| [Structure of Compound E: bis-tert-butyl phenol thioether with O-linked polyol chain] | Compound E | 3c |

Example 4

The effect of Compound A on HDLc levels was assessed using hypercholesterolemic hamsters. Male Golden Syrian hamsters were fed as described in Materials and Methods. Compound A homogenized as described above before adding it to the high cholesterol chow paste and administered as an admixture at the same time each morning for two weeks. At the end of the treatment period the hamsters were fasted in the late afternoon on the day prior to blood collection.

found to a safe concentration for most compounds tested, while concentrations higher than 25 μM were toxic for some compounds. Hence, in most of the experiments, Compound A and probucol were used at a concentration of 12.5 μM.

Figure 2:
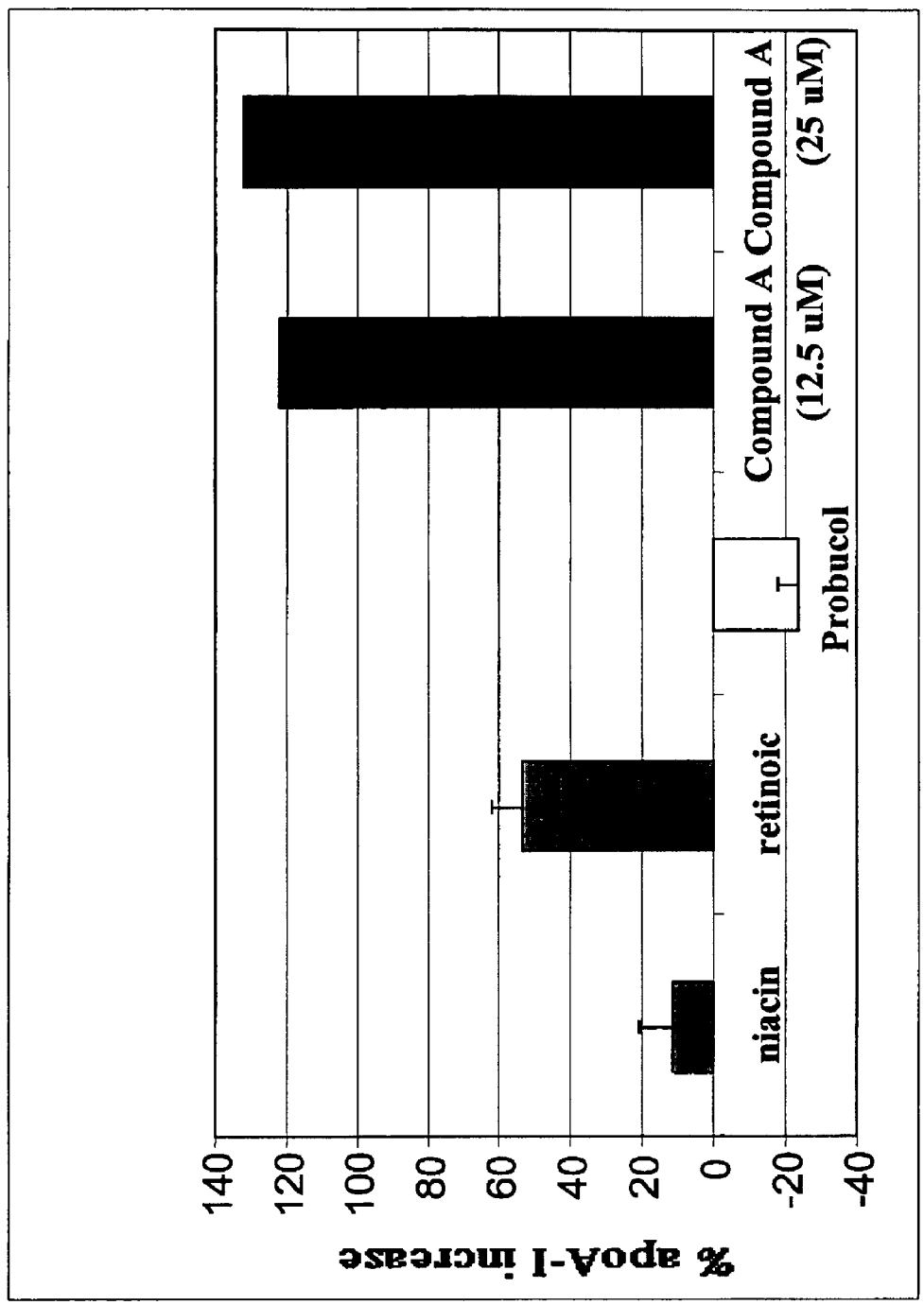
FIG. 2 is a series of bar graphs showing increases in apoAI-HDL by 122.5% and 132.5% in HepG2 cells treated with Compound A.

FIG. 2 shows the percent of apoAI increase after treatment with the indicated compounds compared to control (absence of compounds). Compound A increased apoAI accumulation by 122.5% and 132.5 at concentrations 12.5 μM and 25 μM respectively. Probucol decreased apoAI accumulation by 23%. Retinoic acid at 10 FM was used as positive control and it increased apoAI accumulation by 53.6% as shown by M. Haghpassand and J. B. Moberly (1995) Atherosclerosis 117, 199–207. Niacin at 1 mM also increased apoAI accumulation, consistent with the findings of Kashyap group (Jin, F. et al., *Atheroscler. Thromb. Vasc. Biol.* 17, 2020 (1997)).

Example 6

Figure 3:
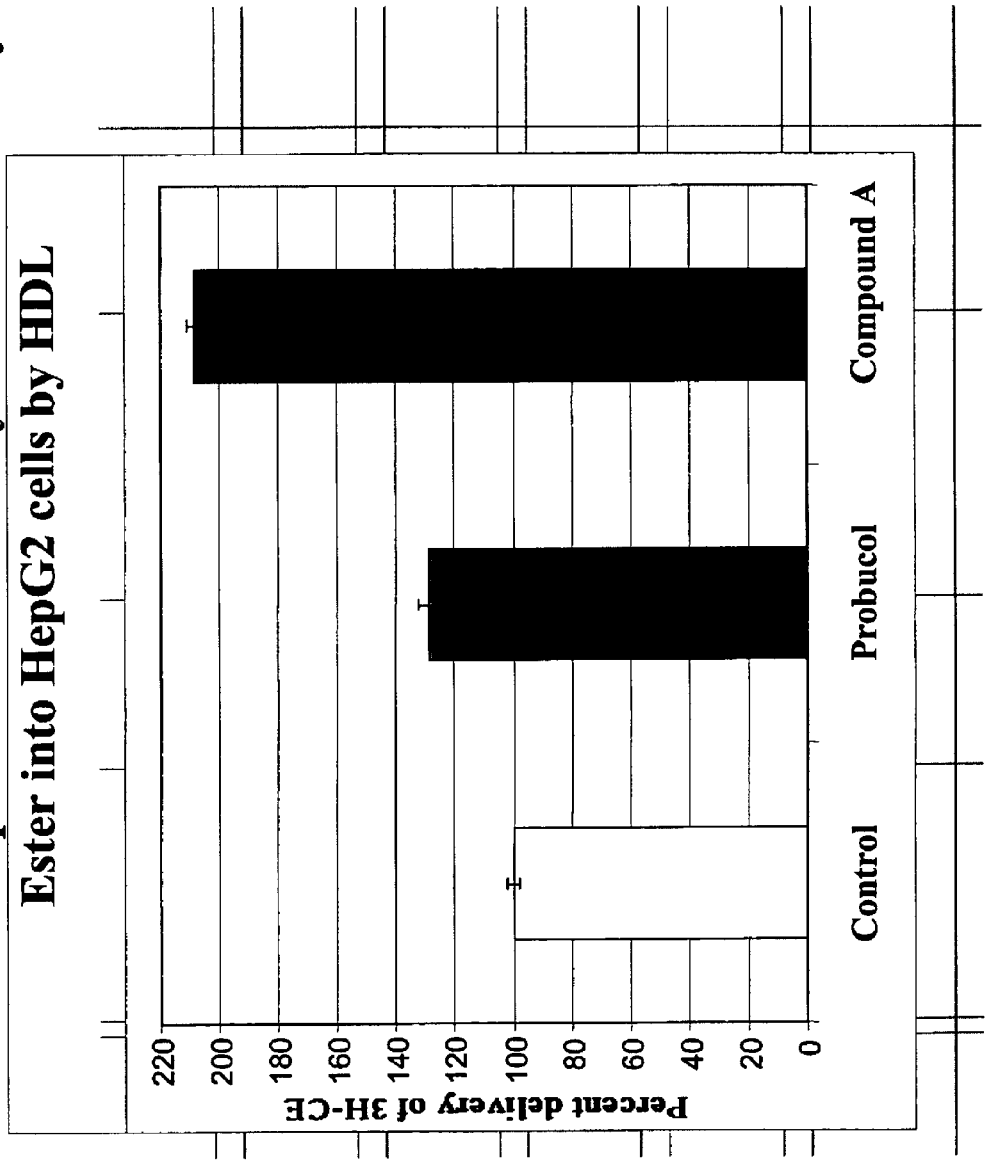
FIG. 3 is a series of bar graphs illustrating that Compound A enhances the clearance of cholesteryl ester in HepG2 cells treated with Compound A.

The role of Compound A in the selective uptake of CE component of HDL was investigated using HepG2 cells. HepG2 cells were cultured as described above and incubated with 50 μg/ml of $^3$[H] CE-HDL particles and compounds for 3.5 h at 37° C. FIG. 3 shows the percent change of $^3$[H] CE delivery to HepG2 cells resulting from treatment with indicated compounds compared to a 100% delivery in the absence of any compound. Niacin at 1 mM did not change the uptake of $^3$[H] CE, as also described by Jin et al. (Jin, F. et al. (1997) *Atheroscler. Thromb Vasc Biol.* 17: 2020–2028). Compound A increased the delivery of $^3$[H]CE to HepG2 cells by 109%, while Probucol had a significantly smaller effect, increasing $^3$[H]CE uptake by 29%.

Example 7

Figure 4:
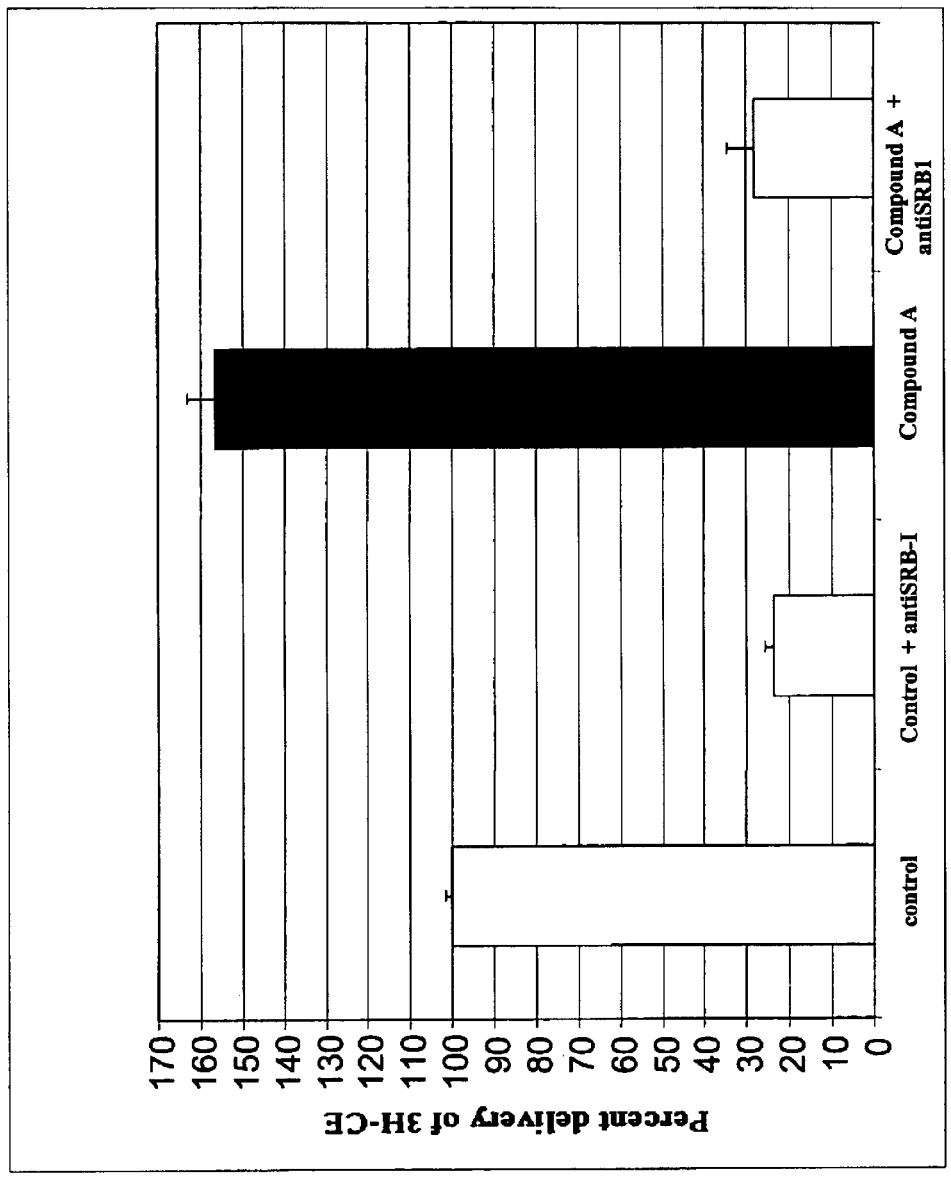
FIG. 4 is a series of bar graphs showing that Compound A increases delivery of cholesteryl ester (CE) in HepG2 cells through the SR-BI/II receptors.

It was important to discern whether or not Compound A was acting through the SR-BI/II receptors to increase the delivery of cholesterol. HepG2 cells were incubated with anti-mouse SR-BI/II antibodies for 45 min. Compound A was then added, and the cells were incubated with 30 μg/ml of $^3$[H] CE-HDL for 3.5 h at 37° C. Anti-mouse SR-BI/II antibodies (1.0 mg/mL) reduced delivery of 3[H] CE by 76%, while Compound A increase the delivery of $^3$[H] CE to HepG2 cells by 56%. Anti SR-BI/II IgG completely blocked the increased delivery of 3[H] CE to cells provoked by Compound A. Further the anti SR-BI/II antibodies decreased the delivery of $^3$[H] CE from 156% to 28% (FIG. 4). These data indicate that Compound A increases the delivery of CE to cells through the SR-BI/II receptors.

Assays have been established to screen for HDLc-elevating compounds, and it has been determined that Compound A is an ideal drug candidate that increases circulating HDLc and improves HDL functionality. In a hepatic model, it has been shown that Compound A increases apoAI-HDL accumulation by 132%. Animal studies have shown that Compound A elevated HDL cholesterol in hypercholesterolemic hamsters by 30% compared to untreated controls after two weeks of treatment at a dose of 150 mg/kg/dL. Both in vitro and in vivo data clearly show that Compound A is a novel HDLc elevating compound. The mechanism of action of Compound A was further investigated.

LDL brings cholesterol from the liver to peripheral tissues for cell utilization; whereas, HDL takes the excess cholesterol from peripheral tissues and artery walls in the form of cholesteryl ester to the liver for its elimination, a process called the reverse cholesterol transport. An elevated HDLc level caused by Compound A must be able to draw more cholesterol from artery walls and in general peripheral cells and bring it to the liver for its elimination. Decreased transport of HDL-cholesterol to the liver would result in accumulation of cholesterol in HDL thereby elevating HDLc. Such a dysfunctional HDL has been shown in transgenic mice overexpressing lecithin cholesteryl acyltransferase (Berard A. M., et al., *Nature Medicine* 3, 744 (1997)). Thus, to ensure the that Compound A was not creating a dysfunctional HDL, it was very important to determine the cholesteryl ester clearance capacity of Compound A from HDL by liver cells.

The data provided shows that Compound A enhances clearance of cholesteryl ester from CE-rich HDL to liver cells by 108%, probably through the SR-BI/II receptors. To demonstrate the role of SR-BI/II HDL receptors, anti SR-BI/II polyclonal antibodies were used to block the receptor site. In the presence of the anti SR-BI/II polyclonal antibodies, cholesteryl ester/ether was reduced by 76%. The SR-BI/II antibodies completely blocked the increase delivery of CE to liver cells caused by Compound A. These results suggest that Compound A greatly enhances elimination of cholesterol (in the form of esters) and functions through the SR-BI/II HDL receptors.

The data provided supports the published concept for two distinct pathways by which cholesterol gets into a cell (Steinberg, D. *Science* 271, 460 (1996)). Cholesteryl esters are selectively delivered to liver, adrenal and ovary cells through the SR-BI/II receptors (Acton, S. L. et al., *Science* 271, 518 (1996); Acton, S. L. et al., *J. Biol. Chem.* 269, 21003 (1994); Glass et al., *Proc. Natl. Acad. Sci. U.S.A.*, 80, 5435 (1983)). Although the nature of the apolipoproteins in HDL may not be important for selective uptake (Pittman, R. C., et al., *J. Biol. Chem.* 262, 2435 (1987)), apoAI is believed to be the preferred ligand for SR-B/II receptors for selective uptake. The next pathway would be the putative apoAI-HDL receptor for HDL whole protein or holoprotein uptake (Steinberg, D., *Science* 271, 460 (1996)). These proteins for the putative HDL receptor such as HB1 and HD2 have been described by Fidge and coworkers (Kurata, H., et al., *J. Atheroscler. Thromb.*, 4, 112 (1998)). An identical receptor, cubilin, that endocytoses HDL in kidney cells has been identified (Hammad, S. M., et al. *Proc. Natl. Acad. Sci.* 96,10158 (1999)).

Other probucol derivatives seem to interact with HDL and increase its binding to the SR-BI/II receptors, probably, by increasing the affinity of apoAI binding to SR-BI. Detailed studies in the mechanism of these other derivatives shows that the compounds bind to HDL particles, and affect the interaction at the HDL-cell surface protein level, and specifically affecting the SR-BI/II receptors, and possibly the candidate HDL-binding proteins, HB1 and HD2 described by Fidge and coworkers (Kurata. H., et al., *J. Atheroscler. Thromb.*, 4, 112 (1998)).

Niacin and probucol were used in these experiments as controls. Niacin reduces hepatic clearance of apoAI-HDL, and probucol increases selective uptake of cholesteryl esters. A very modest reduction of HDL-CE holoprotein clearance in the presence of niacin at 1 mM was observed as described by Kashyap and co-workers (Jin, F. Y., et al., Arterioscler. Thromb. Vasc. Biol. 17, 2020 (1997)). This modest reduction could account for the observed 10% increase in circulating apoAI-HDL. Importantly, niacin had no effect on the clearance of HDL3 holoproteins.

Comparative Example 1

Figure 5:
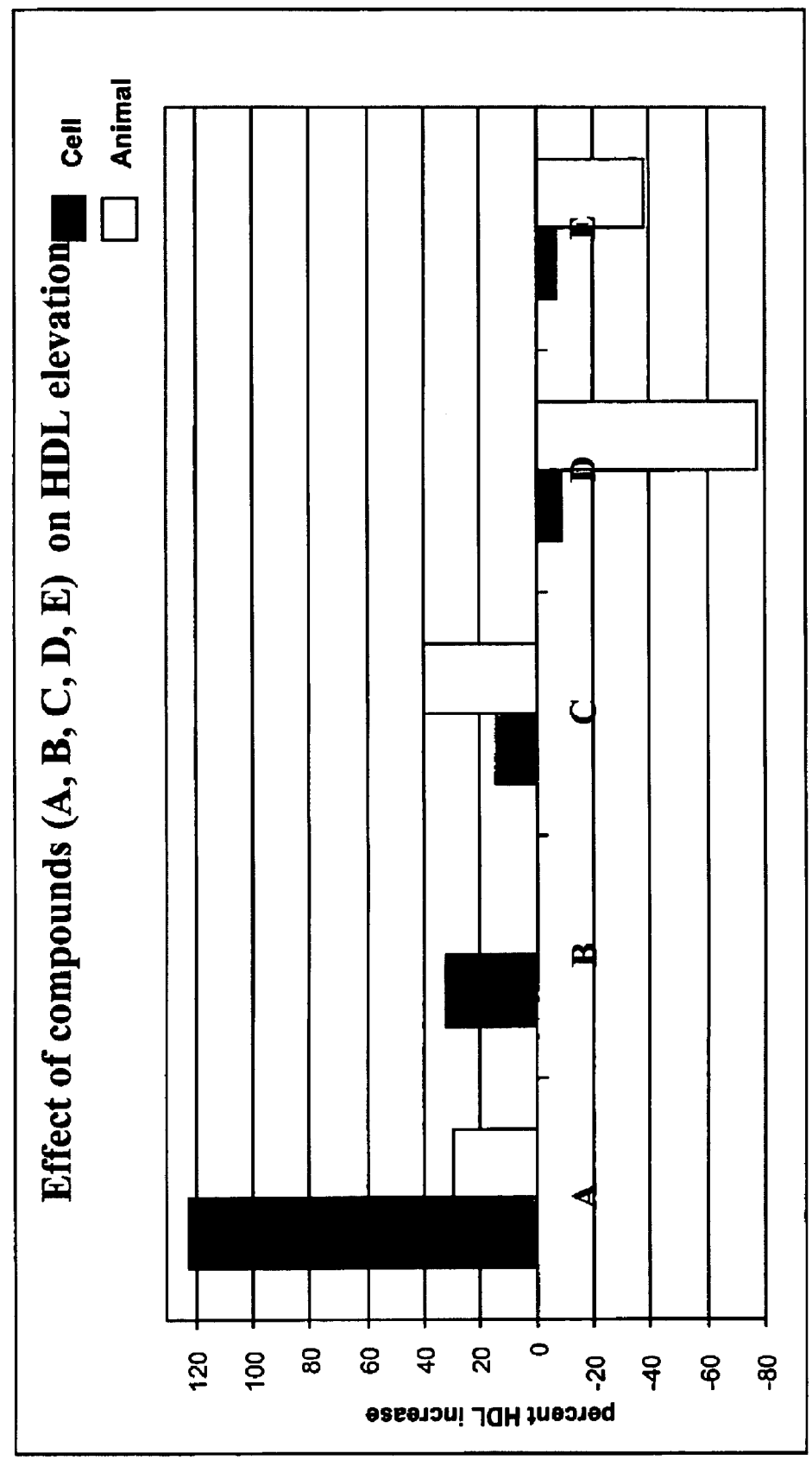
FIG. 5 is a series of bar graphs comparing (a) the effects of compounds (A, B, C, D, E) on apoAI-HDL elevation in cells measured using the cell-based screen as example 3, and (b) the effects of compounds (A, B, C, D, E) on HDL cholesterol measured in hypercholesterolemic hamsters as described in example 4.

HDLc Elevating Ability of Active Compounds A, B, and C Versus Inactive Compounds D and E In this comparative example, the ability of Compounds A, B, and C to raise apoAI-HDL in cells as measured using the cell-based screening methods described in example 3, was compared to the related ethers D and E. The results of the comparison are shown in FIG. 5. FIG. 5 shows the percent change in apoAI-HDL after treatment with 12.5 micromolar of the indicated compounds compared to control (absence of compounds) in the cell-based screening assay. In this comparison, Compound A exhibited the greatest percent increase in apoAI-HDL (122%), compound B exhibited an approximate 30% increase in apoAI-HDL and Compound C exhibited about a 15% increase. In contrast, Compounds D and E lowered apoAI-HDL by about 10%.

The ability of compounds (A, B, C, D, E) to raise HDL cholesterol was also measured in hypercholesterolemic hamsters using methods described in Example 4. FIG. 5 shows the percent change of HDL cholesterol in hypercholesterolemic hamsters by the indicated compounds at a dose of 150 mg/kg/d compared to untreated controls after two weeks of treatment. Compound C exhibited the greatest percent increase in HDLc (40%) in hamsters, and compound A exhibited an approximate 30% increase in HDLc. In contrast, Compounds D and E lowered HDLc by nearly 80% and 40%, respectively.

Comparative Example 2

Probucol

Probucol, a widely prescribed and potent cholesterol-lowering agent in both LDL and HDL fractions will selectively remove cholesteryl esters by a SR-BI-dependent mechanism (Rinninger, F., et al., Arterioscler. Thromb. Vasc. Biol. 19, 1325 (1999)) resulting in significant improvement in tendious xanthomas or atheromatous regions of the aorta in both humans and experimental animals (Yamamoto, A., et al., Am. J. Cardiol. 57, 29 (1986); Kita, T., et al., Proc. Natl. Acad. Sci. U.S.A. 84, 5928 (1987)). It has been found that probucol not only increased selective uptake of cholesteryl esters to the liver, but it also reduced HDL holoprotein uptake. The effect of probucol on both processes was significantly lower than the effects of the compounds of the current invention. The remarkable difference was found at the production level. While compounds of the current invention have no effect on newly synthesized apoAI, probucol reduced the synthesis of apoAI. As a result, the net effect of probucol was lowering of circulating HDLc levels; whereas, the net effect of the compounds of the current invention was to increase circulating HDLc levels. Compound A works through a unique mechanism of HDL elevation and is an ideal drug that increases the delivery of cholesteryl ester to the liver for its elimination.

Modifications and variations of the present invention will be obvious to those skilled in the art from the foregoing. All of these embodiments are considered to fall within the scope of this invention.

What is claimed is:

1. A compound of the formula

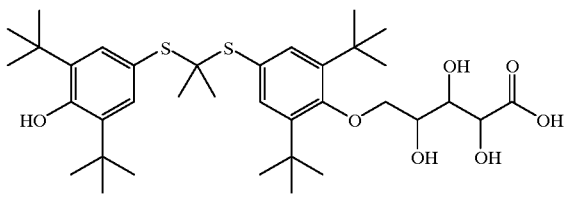

or its pharmaceutically acceptable salt or prodrug.

2. A compound of the formula:

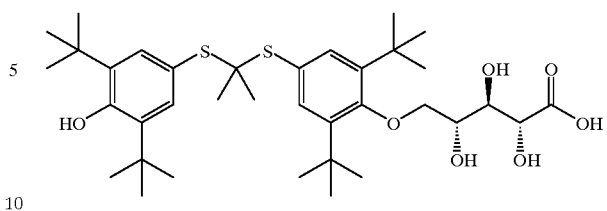

or its pharmaceutically acceptable salt or prodrug.

3. A method for increasing high density lipoprotein cholesterol level in a host comprising administering an effective amount of the compound of claim 1.

4. A method to improve the functionality of circulating high density lipoprotein in a host, comprising administering an effective amount of the compound of claim 1.

5. A method for increasing high density lipoprotein cholesterol level in a host comprising administering an effective amount of the compound of claim 2.

6. A method to improve the functionality of circulating high density lipoprotein in a host, comprising administering an effective amount of the compound of claim 2.

7. A pharmaceutical composition comprising a pharmaceutically acceptable carrier or diluent and a therapeutically effective amount of

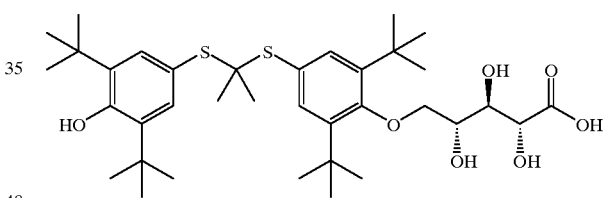

or a pharmaceutically acceptable salt thereof.

8. The pharmaceutical composition of claim 7 further comprising an IBAT inhibitor.

9. The pharmaceutical composition of claim 7 further comprising a statin.

10. The pharmaceutical composition of claim 9 wherein the statin is selected from the group consisting of lovastatin, simvastitin, pravastatin, fluvastatin, and atorvastatin.

11. The pharmaceutical composition of claim 7 further comprising a CETP inhibitor.

12. The pharmaceutical composition of claim 7 further comprising a fibrate.

13. The pharmaceutical composition of claim 7 further comprising nicotinic acid.

14. The pharmaceutical composition of claim 7 further comprising a compound selected from group consisting of probucol, nicotinic acid, platelet aggregation inhibitors, aspirin, coumadin, varapmil, diltiazem, nifedipine, an ACE inhibitor, captopril enalopril, propanalol, terbutalol, labetalol, ibuprofen, indomethacin, fenoprofen, mefenamic acid, flufenamic acid, sulinda, and a corticosteroid.

15. A pharmaceutical composition comprising a pharmaceutically acceptable carrier or diluent and a therapeutically effective amount of

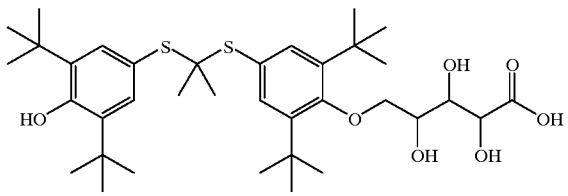

or a pharmaceutically acceptable salt thereof.

16. The pharmaceutical composition of claim 15 further comprising a statin.

17. The pharmaceutical composition of claim 16 wherein the statin is selected from the group consisting of lovastatin, simvastitin, pravastatin, fluvastatin, and atorvastatin.

18. The pharmaceutical composition of claim 15 further comprising a CETP inhibitor.

19. The pharmaceutical composition of claim 15 further comprising a fibrate.

20. The pharmaceutical composition of claim 15 further comprising nicotinic acid.

21. The pharmaceutical composition of claim 15 further comprising a compound selected from group consisting of probucol, nicotinic acid, platelet aggregation inhibitors, aspirin, coumadin, varapmil, diltiazem, nifedipine, an ACE inhibitor, captopril enalopril, propanalol, terbutalol, labetalol, ibuprofen, indomethacin, fenoprofen, mefenamic acid, flufenamic acid, sulinda, and a corticosteroid.

22. A method to treat a cardiovascular disease in a subject, which method comprises administering to said subject a therapeutically-effective amount of a compound of claim 1 or a pharmaceutically acceptable salt thereof.

23. The method of claim 22 wherein the cardiovascular disease is atherosclerosis.

24. The method of claim 22 wherein the cardiovascular disease is hypercholesterolemia.

25. A method to treat a cardiovascular disease in a subject, which method comprises administering to said subject a therapeutically-effective amount of a compound of claim 2 or a pharmaceutically acceptable salt thereof.

26. The method of claim 25 wherein the cardiovascular disease is atherosclerosis.

27. The method of claim 25 wherein the cardiovascular disease is hypercholesterolemia.

28. The method of claim 3 wherein the host is a human.

29. The method of claim 4 wherein the host is a human.

30. The method of claim 5 wherein the host is a human.

31. The method of claim 6 wherein the host is a human.

32. The method of claim 22 wherein the subject is a human.

33. The method of claim 25 wherein the subject is a human.

* * * * *